ись
United States Patent
Sato et al.

(10) Patent No.: US 8,214,017 B2
(45) Date of Patent: Jul. 3, 2012

(54) CAPSULE GUIDING SYSTEM

(75) Inventors: Ryoji Sato, Fuchu (JP); Atsushi Kimura, Akiruno (JP); Akio Uchiyama, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 628 days.

(21) Appl. No.: 12/400,240

(22) Filed: Mar. 9, 2009

(65) Prior Publication Data
US 2009/0227864 A1 Sep. 10, 2009

(30) Foreign Application Priority Data
Mar. 10, 2008 (JP) ................................. 2008-059287

(51) Int. Cl.
*A61B 5/05* (2006.01)
(52) U.S. Cl. ....................................... 600/424; 345/158
(58) Field of Classification Search .................. 600/424; 345/618, 158, 162
See application file for complete search history.

(56) References Cited

U.S. PATENT DOCUMENTS

| | | | | |
|---|---|---|---|---|
| 5,134,390 | A * | 7/1992 | Kishimoto et al. | 345/659 |
| 6,038,467 | A * | 3/2000 | De Bliek et al. | 600/424 |
| 7,117,009 | B2 * | 10/2006 | Wong et al. | 455/556.1 |
| 2002/0058870 | A1 * | 5/2002 | Panescu et al. | 600/424 |
| 2003/0214580 | A1 | 11/2003 | Iddan | |
| 2005/0020910 | A1 * | 1/2005 | Quadling et al. | 600/424 |
| 2005/0216231 | A1 | 9/2005 | Aoki et al. | |
| 2006/0063974 | A1 | 3/2006 | Uchiyama et al. | |

FOREIGN PATENT DOCUMENTS

| | | |
|---|---|---|
| CN | 101022758 A | 8/2007 |
| DE | 10 2006 014 626 A1 | 10/2007 |
| JP | 2007-216040 | 8/2007 |
| WO | WO 2006/033306 A1 | 3/2006 |
| WO | WO 2007/113055 A2 | 10/2007 |

* cited by examiner

*Primary Examiner* — Jonathan Cwern
(74) *Attorney, Agent, or Firm* — Scully, Scott, Murphy & Presser, P.C.

(57) ABSTRACT

A capsule guiding system includes a magnetic guiding unit, a displaying unit, an operation unit, and a control unit. The magnetic guiding unit guides, using magnetic force, a capsule-shaped medical apparatus introduced inside a subject. The displaying unit displays an image of the subject and an image of the capsule-shaped medical apparatus as an overlapped image, and changes relative position and relative direction between the two images as the capsule-shaped medical apparatus is guided by the magnetic guiding unit. The operation unit inputs coordinate information which specifies movement direction of the capsule-shaped medical apparatus. The control unit adjusts coordinate system of the displaying unit and coordinate system of the operation unit to be consistent with each other, transforms the coordinate information input from the operation unit into the coordinate system of the magnetic guiding unit, and controls the guiding of the capsule-shaped medical apparatus based on the transformed coordinate information.

7 Claims, 9 Drawing Sheets

CAPSULE-SHAPED MEDICAL APPARATUS 2

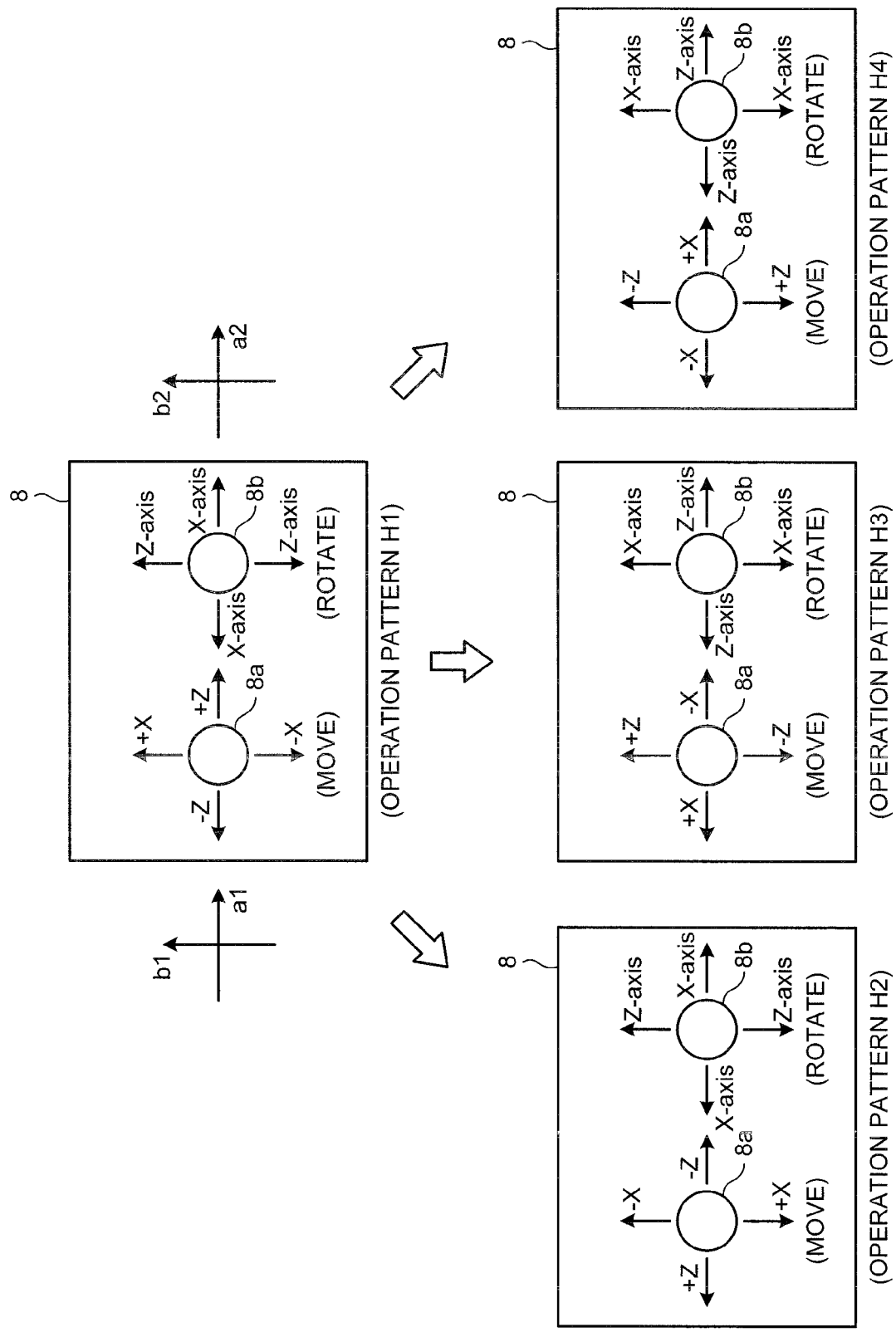

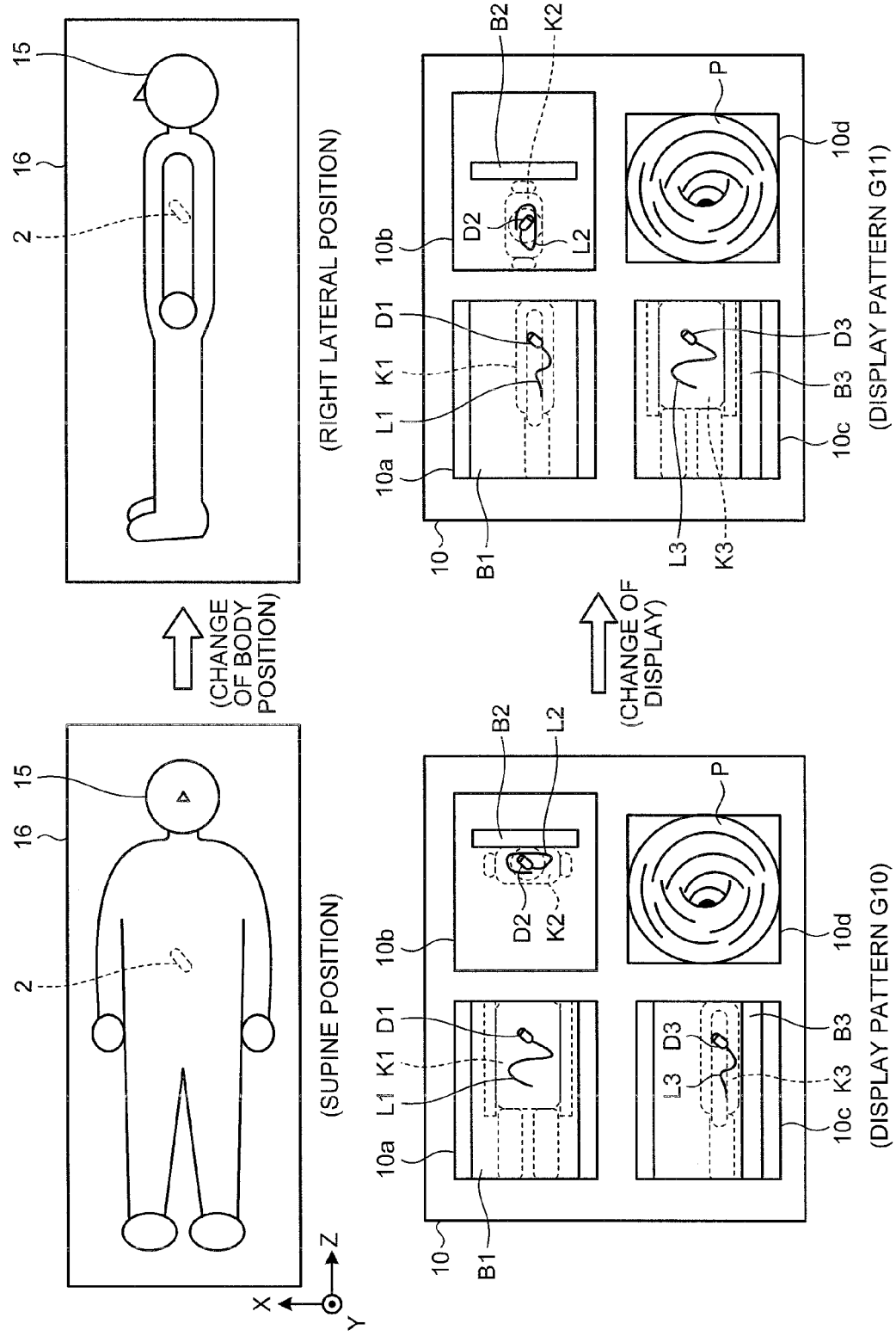

CAPSULE GUIDING SYSTEM

CROSS-REFERENCE TO RELATED APPLICATIONS

This application is based upon and claims the benefit of priority from Japanese Patent Application No. 2008-059287, filed Mar. 10, 2008, the entire contents of which are incorporated herein by reference.

BACKGROUND OF THE INVENTION

1. Field of the Invention

The present invention relates to a capsule guiding system which guides a capsule-shaped medical apparatus introduced inside a subject, e.g., a patient.

2. Description of the Related Art

Conventionally, there has been a capsule-shaped medical apparatus which can be introduced inside a digestive tract of a subject, e.g., a patient. The capsule-shaped medical apparatus is swallowed from a mouth of the subject, and picks up in-vivo information such as images of insides of organs of the subject (hereinafter, "in-vivo images") while moving inside the digestive tract due to a peristalsis or the like. The capsule-shaped medical apparatus then wirelessly transmits the obtained in-vivo information to a receiver which is arranged outside the subject. The capsule-shaped medical apparatus starts to obtain the in-vivo information of the subject when introduced inside the digestive tract of the subject, and continues to do so until naturally excreted outside the subject.

Recently, there has been proposed a capsule guiding system which guides the capsule-shaped medical apparatus introduced inside the subject by magnetic force. For example, Japanese Patent Application Laid-Open No. 2007-216040 discloses a capsule guiding system (i.e., a medical apparatus guiding system) in which a capsule-shaped medical apparatus whose capsule-shaped container contains a magnet magnetized in a radial direction and has spiral projections on an outer surface thereof is introduced inside the digestive tract of the subject, and then rotating magnetic field generated by a rotating magnetic field generating unit is applied to the capsule-shaped medical apparatus inside the subject so that the capsule-shaped medical apparatus is guided to a desired position inside the subject.

In general, the capsule guiding system includes a displaying apparatus which displays in-vivo images and the like captured by the capsule-shaped medical apparatus inside the subject, and an operating apparatus, e.g., a joystick for operating the magnetic guiding of the capsule-shaped medical apparatus inside the subject. When a user (i.e., an operator) such as a doctor and a nurse uses the capsule guiding system to magnetically guide the capsule-shaped medical apparatus inside the subject, the displaying apparatus displays thereon a schematic image showing a schematic body shape of the subject and a schematic image showing an outer shape of the capsule-shaped medical apparatus, and the user operates the operating apparatus with reference to a position and a longitudinal direction of the schematic image of the capsule-shaped medical apparatus in the schematic image of the subject which is displayed on the displaying apparatus. In this case, the user can view a relative movement direction or a relative rotation direction of the schematic image of the capsule-shaped medical apparatus relative to the schematic image of the subject displayed on the displaying apparatus, and thus can understand a magnetic guiding direction of the capsule-shaped medical apparatus inside the subject.

SUMMARY OF THE INVENTION

A capsule guiding system according to an aspect of the present invention includes a magnetic guiding unit which guides a capsule-shaped medical apparatus introduced inside a subject by magnetic force, a displaying unit which displays a subject image showing the subject and a capsule image showing the capsule-shaped medical apparatus as an overlapped image and changes a relative position or a relative direction of the subject image and the capsule image according to a guiding of the capsule-shaped medical apparatus performed by the magnetic guiding unit, an operation unit which inputs coordinate information specifying a movement direction of the capsule-shaped medical apparatus, and operates the guiding of the capsule-shaped medical apparatus performed by the magnetic guiding unit, and a control unit which adjusts a coordinate system of a display screen of the displaying unit and a coordinate system of an input operation direction of the operation unit to be consistent with each other, performs a coordinate transformation which transforms the coordinate information input by the operation unit into the coordinate system of the magnetic guiding unit, and controls the guiding of the capsule-shaped medical apparatus based on the coordinate information on which the coordinate transformation is performed.

A medical apparatus guiding system according to an aspect of the present invention includes a medical apparatus which is introduced inside a subject, a guiding apparatus which guides the medical apparatus, a position-direction detecting apparatus which detects a position and a direction of the medical apparatus relative to the guiding apparatus, a man-machine interface unit which includes an input apparatus which generates instruction information to be transmitted to the guiding apparatus, and a displaying apparatus which displays at least a detection result of the position-direction detecting apparatus, and a positional relation selecting unit which selects a direction of the guiding apparatus and a positional relation of the man-machine interface unit. The medical apparatus guiding system changes an operation direction of the input apparatus or display of the displaying apparatus or both based on a selection result of the positional relation selecting unit.

A medical apparatus guiding system according to an aspect of the present invention includes, a medical apparatus which is introduced inside a subject, a guiding apparatus which guides the medical apparatus, a position-direction detecting apparatus which detects a position and a direction of the medical apparatus relative to the guiding apparatus, a man-machine interface unit which includes an input apparatus which generates instruction information to be transmitted to the guiding apparatus, and a displaying apparatus which displays at least a detection result of the position-direction detecting apparatus, and a positional relation determining unit which determines a positional relation between a direction of the guiding apparatus and a direction of the man-machine interface unit. The medical apparatus guiding system changes an operation direction of the input apparatus or display of the displaying apparatus or both based on output of the positional relation determining unit.

A medical apparatus guiding system according to an aspect of the present invention includes a medical apparatus which is introduced inside a subject, a guiding apparatus which guides the medical apparatus, a position-direction detecting apparatus which detects a position and a direction of the medical apparatus relative to the guiding apparatus, and a man-machine interface unit which includes an input apparatus which generates instruction information to be transmitted to the guiding apparatus, and a displaying apparatus which displays at least a detection result of the position-direction detecting apparatus. The medical apparatus guiding system changes an operation direction of the input apparatus or display of the displaying apparatus or both based on the direction of the medical apparatus detected by the position-direction detecting apparatus and a direction of the man-machine interface unit.

A displaying system according to an aspect of the present invention includes position sensors which are arranged on the subject, and measure a body position of the subject, an introduced apparatus which is introduced inside the subject, an introduced-apparatus-position detector which detects a position of the introduced apparatus, a display which displays a detection result of the position sensors and a detection result of the introduced-apparatus-position detector, a storage which continuously stores position information of the guiding apparatus detected by the introduced-apparatus-position detector, and a display controller which changes a display state of the subject on the display based on a measurement result of the position sensors, and displays the position information of the introduced apparatus stored in the storage on the display.

A displaying system of a guiding apparatus according to an aspect of the present invention includes an introduced apparatus which is introduced inside the subject, a guiding apparatus which guides the introduced apparatus, body position sensors which measure a body position of the subject relative to the guiding apparatus, an introduced-apparatus-position detector which measures a position of the introduced apparatus relative to the guiding apparatus, a display which displays the body position of the subject and the position of the introduced apparatus relative to the guiding apparatus, and a storage which continuously stores position information of the introduced apparatus detected by the introduced-apparatus-position detector. The position information of the introduced apparatus which is stored in the storage is displayed on the display.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a schematic illustration of a correspondence relation between the input operation direction of the operation unit and the movement direction of the capsule-shaped medical apparatus; and FIG. 10 shows a schematic concrete explanation of change in display information of the displaying apparatus according to the change of body position of the subject.

DETAILED DESCRIPTION OF THE PREFERRED EMBODIMENTS

Exemplary embodiments of a capsule guiding system of the present invention are described below. A capsule-shaped medical apparatus which captures in-vivo images of a subject is described below as an example of a capsule-shaped medical apparatus of the capsule guiding system according to the present invention. The embodiments, however, do not intend to limit the scope of the invention.

Figure 1:
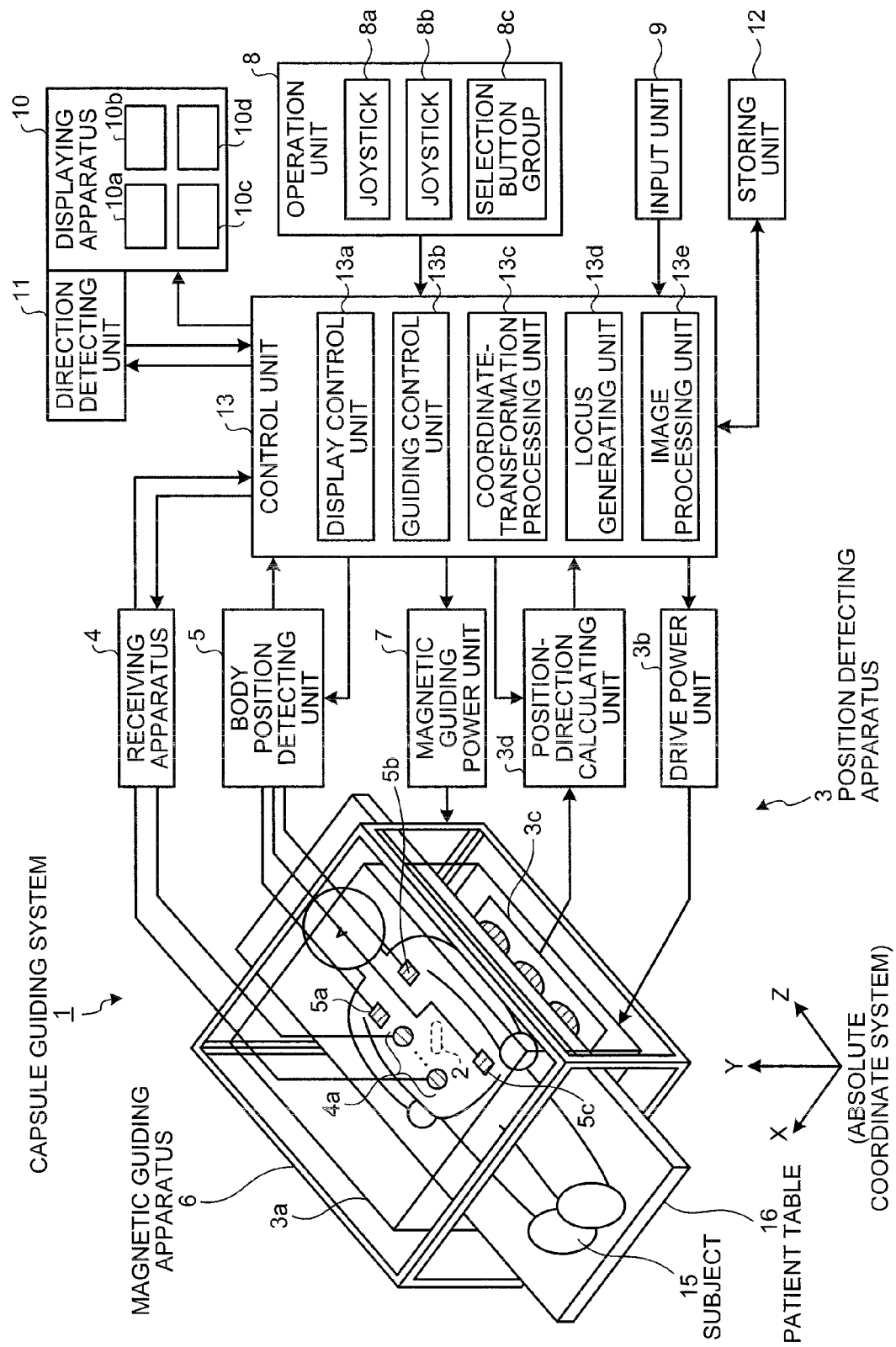
FIG. 1 is an exemplary block diagram of schematic configuration of a capsule guiding system according to a first embodiment of the present invention.

FIG. 1 is an exemplary block diagram of schematic configuration of a capsule guiding system according to a first embodiment of the present invention. As shown in FIG. 1, a capsule guiding system 1 according to the first embodiment includes a capsule-shaped medical apparatus 2 which is introduced inside a digestive tract of a subject 15, e.g., a patient, a position detecting apparatus 3 which detects a position and the like of the capsule-shaped medical apparatus 2 inside the body of the subject 15, a receiving apparatus 4 which receives in-vivo images of the subject 15 taken by the capsule-shaped medical apparatus 2, and a body position detecting unit 5 which detects a body position of the subject 15 who lies on a patient table 16, e.g., a bed. Further, the capsule guiding system 1 includes a magnetic guiding apparatus 6 which guides the capsule-shaped medical apparatus 2 inside the subject 15 by magnetic force, a magnetic guiding power unit 7 which supplies power for the magnetic guiding apparatus 6, and an operation unit 8 which operates a guiding which is performed magnetically (hereinafter, "magnetic guiding") on the capsule-shaped medical apparatus 2 by the magnetic guiding apparatus 6. Further, the capsule guiding system 1 includes an input unit 9 which inputs various information, a displaying apparatus 10 which displays various information such as in-vivo images of the subject 15, a direction detecting unit 11 which detects a relative direction of the displaying apparatus 10 to the magnetic guiding apparatus 6, a storing unit 12 which stores various information such as a group of in-vivo images of the subject 15, and a control unit 13 which controls each component of the capsule guiding system 1.

The capsule-shaped medical apparatus 2 is a medical apparatus having a shape of a capsule, obtains in-vivo images (an example of information inside the subject) of the subject, and has an imaging function and a wireless communication function. Specifically, the capsule-shaped medical apparatus 2 is introduced inside the body of the subject 15, e.g., a patient, and continuously captures the in-vivo images while moving inside the digestive tract of the subject 15. In each capturing of the in-vivo image of the subject 15, the capsule-shaped medical apparatus 2 wirelessly transmits an image signal including the captured in-vivo image to the receiving apparatus 4 which is arranged outside the subject 15. Further, the capsule-shaped medical apparatus 2 contains a magnetic body, e.g., a permanent magnet or an electromagnet (hereinafter, both may be simply referred to as "magnet"), and is magnetically guided according to a magnetic field generated by the magnetic guiding apparatus 6.

The position detecting apparatus 3 detects a position and a direction of the capsule-shaped medical apparatus 2 inside the body of the subject 15. The position detecting apparatus 3 includes a drive-magnetic-field generating unit 3a which generates a magnetic field for detecting the position and the direction of the capsule-shaped medical apparatus 2, a drive power unit 3b which supplies power for the drive-magnetic-field generating unit 3a, a magnetic field detecting unit 3c which detects a magnetic field from the capsule-shaped medical apparatus 2, and a position-direction calculating unit 3d which calculates the position and the direction of the capsule-shaped medical apparatus 2 inside the subject 15.

The drive-magnetic-field generating unit 3a is realized by a coil and the like which generates a magnetic field in the direction of each axis of an absolute coordinate system of the magnetic guiding apparatus 6 described later. The drive-magnetic-field generating unit 3a generates the magnetic field in the direction of each axis of the absolute coordinate system by using power (specifically, alternate current) supplied from the drive power unit 3b, and applies the generated magnetic field to the capsule-shaped medical apparatus 2. The drive-magnetic-field generating unit 3a generates a guiding magnetic field in the capsule-shaped medical apparatus 2 by the magnetic field which is applied to the capsule-shaped medical apparatus 2.

The drive power unit 3b supplies for the drive-magnetic-field generating unit 3a the alternate current which is needed for generating magnetic field to be applied to the capsule-shaped medical apparatus 2 under the control of the control unit 13. The direction and strength of the magnetic field generated by the drive-magnetic-field generating unit 3a described above are controlled by the alternate current (an amount of power from the drive power unit 3b) supplied from the drive power unit 3b.

The magnetic field detecting unit 3c is realized, for example, by plural detection coils which are arranged in a grid, and detects the guiding magnetic field released from the capsule-shaped medical apparatus 2 because of the magnetic field generated by the drive-magnetic-field generating unit 3a described above. The magnetic field detecting unit 3c transmits a detection result of the guiding magnetic field from the capsule-shaped medical apparatus 2 to the position-direction calculating unit 3d.

The position-direction calculating unit 3d calculates the position and the direction of the capsule-shaped medical apparatus 2 inside the subject 15. Specifically, the position-direction calculating unit 3d calculates space coordinates and a direction vector (vectors in each of a longitudinal direction and a radial direction of the capsule-shaped medical apparatus 2) of the capsule-shaped medical apparatus 2 in the absolute coordinate system of the magnetic guiding apparatus 6 every time the position-direction calculating unit 3d obtains from the magnetic field detecting unit 3c, the detection result of the guiding magnetic field which is released from the capsule-shaped medical apparatus 2. The position-direction calculating unit 3d calculates a three-dimensional current position and a three-dimensional current direction of the capsule-shaped medical apparatus 2 inside the subject 15 based on the space coordinates and the direction vector of the capsule-shaped medical apparatus 2 in the absolute coordinate system. The position-direction calculating unit 3d transmits the current position information and the current direction information of the capsule-shaped medical apparatus 2 calculated as above to the control unit 13.

The direction of the capsule-shaped medical apparatus 2 calculated by the position-direction calculating unit 3d is determined by a state of rotation around the longitudinal axis of the capsule-shaped medical apparatus 2. The state above is determined by the longitudinal direction of the capsule-shaped container of the capsule-shaped medical apparatus 2, and the radial direction of the capsule-shaped container (i.e., directions along two orthogonal axes which are perpendicular to the longitudinal direction of the capsule-shaped container).

The receiving apparatus 4 includes plural receiving antennas 4a which receive wireless signals from the capsule-shaped medical apparatus 2. The receiving apparatus 4 receives the wireless signals from the capsule-shaped medical apparatus 2 via the receiving antennas 4a. Specifically, the receiving antennas 4a are separately arranged on a body surface of the subject 15, and receive the wireless signals from the capsule-shaped medical apparatus 2 which moves inside the digestive tract of the subject 15. The receiving apparatus 4 selects one of the receiving antennas 4a which receives strongest electric field, and receives the wireless signals from the capsule-shaped medical apparatus 2 via the selected receiving antenna. The receiving apparatus 4 performs a demodulation process and the like on the wireless signal received from the capsule-shaped medical apparatus 2 to thereby obtain the image signal (i.e., the image signal including the in-vivo images of the subject 15 captured by the capsule-shaped medical apparatus 2) corresponding to the wireless signal, and transmits the obtained image signal to the control unit 13.

The body position detecting unit 5 detects the body position of the subject 15 who contains the capsule-shaped medical apparatus 2 inside his body. Specifically, the body position detecting unit 5 includes three detection coils 5a to 5c which are arranged on the body surface of the subject 15. The detection coils 5a to 5c are arranged near the sides of the subject 15, and near the lower abdomen of the subject 15, respectively, and detect the magnetic field generated by the drive-magnetic-field generating unit 3a or the magnetic guiding apparatus 6. The body position detecting unit 5 obtains a magnetic-field detection result of the detection coils 5a to 5c, and calculates each of positional coordinates and direction vectors of the detection coils 5a to 5c (e.g., normal vectors of the detection coils 5a to 5c) in the absolute coordinate system of the magnetic guiding apparatus 6 based on the obtained magnetic-field detection result.

Each of the positional coordinates and the direction vectors of the detection coils 5a to 5c calculated by the body position detecting unit 5 is maintained relatively to the subject 15, and changes according to change of the body position of the subject 15. In this case, the position and the direction (i.e., the body position of the subject 15) of an upper body of the subject 15 in the absolute coordinate system of the magnetic guiding apparatus 6 are determined based on each of the positional coordinates of the detection coils 5a to 5c. The body position detecting unit 5 detects each of the positional coordinates of the detection coils 5a to 5c as the information which specifies the body position of the subject 15, and transmits a detection result of the body position to the control unit 13.

The positions where the detection coils 5a to 5c of the body position detecting unit 5 are arranged are not limited to be the neighborhood of both sides and the lower abdomen, and may be arbitrary positions on the body surface of the subject 15 as long as the detection coils 5a to 5c are not arranged in a straight line. It is preferable, however, that the detection coils 5a to 5c be arranged at positions on the body surface where the position and the direction thereof changes sensitively according to the change of body position of the subject 15 (e.g., positions near sides of the upper body), and further that distance among the detection coils 5a to 5c be as long as possible. The number of the detection coils arranged on the body surface of the subject is not limited to three, and may be four or more.

The magnetic guiding apparatus 6 is realized by plural electromagnets, e.g., Helmholtz coils which are combined together, and magnetically guides the capsule-shaped medical apparatus 2 inside the subject 15. Specifically, the absolute coordinate system, i.e., a triaxial orthogonal coordinate system formed by three orthogonal axes (X-axis, Y-axis, and Z-axis) is defined, and the magnetic guiding apparatus 6 generates the magnetic field of desired strength along each of the axes (along X-axis, Y-axis, and Z-axis) of the absolute coordinate system. The magnetic guiding apparatus 6 positions the subject 15 lying on the patient table 16 in the inner space (i.e., the inner space surrounded by the plural electromagnets of the magnetic guiding apparatus 6) of the absolute coordinate system, applies the three-dimensional rotating magnetic field or a three-dimensional gradient magnetic field generated by the magnetic field along each of the axes of the absolute coordinate system to the capsule-shaped medical apparatus 2 inside the subject 15, and thereby operating, i.e., magnetically guiding the capsule-shaped medical apparatus 2. The magnetic field (i.e., the rotating magnetic field and the gradient magnetic field) along each of the axes in the absolute coordinate system generated by the magnetic guiding apparatus 6 is controlled by the alternate current supplied from the magnetic guiding power unit 7 (i.e., by the amount of electricity from the magnetic guiding power unit 7). The patient table 16 includes a drive unit (not shown) which can move the patient table 16 along Z-axis of the absolute coordinate system. The patient table 16 is moved along Z-axis of the absolute coordinate system to move the subject 15 into or out of the inner space of the absolute coordinate system.

The absolute coordinate system may be a triaxial orthogonal coordinate system which is defined based on the magnetic guiding apparatus 6 (i.e., which is fixated on the magnetic guiding apparatus 6), and, further, may be a triaxial orthogonal coordinate system which is fixated on the subject 15 who contains the capsule-shaped medical apparatus 2 inside the digestive tract, or a triaxial orthogonal coordinate system which is fixated on the patient table 16 on which the subject 15 is positioned.

The magnetic guiding power unit 7 supplies the alternate current for the electromagnet of the magnetic guiding apparatus 6 under the control of the control unit 13, whereby the magnetic guiding apparatus 6 is made to release the magnetic field (the magnetic field along each of the axes of the absolute coordinate system of the magnetic guiding apparatus 6) needed for the magnetic guiding of the capsule-shaped medical apparatus 2 inside the subject 15.

The operation unit 8 operates the magnetic guiding of the capsule-shaped medical apparatus 2 which is performed by the magnetic guiding apparatus 6. Specifically, the operation unit 8 includes two joysticks 8a, 8b for operating the three-dimensional magnetic guiding of the capsule-shaped medical apparatus 2 in the absolute coordinate system of the magnetic guiding apparatus 6, and a selection button group 8c for selecting an operation screen for the magnetic guiding of the capsule-shaped medical apparatus 2 from a display screen of the displaying apparatus 10 described later. The operation unit 8 inputs operation information for the magnetic guiding of the capsule-shaped medical apparatus 2 performed by the magnetic guiding apparatus 6 to the control unit 13 based on input operation of the joysticks 8a, 8b by the user (operator) such as a doctor and a nurse. The operation information of the magnetic guiding which is input from the operation unit 8 specifies a movement direction and a movement speed of the capsule-shaped medical apparatus 2 which is magnetically guided by the magnetic guiding apparatus 6.

The input unit 9 is realized by input devices such as a keyboard and a mouse, and inputs various information to the control unit 13 based on the input operation by the user such as a doctor and a nurse. The various information which is input to the control unit 13 from the input unit 9 is, for example, instruction information which includes instructions for the control unit 13, patient information of the subject, and examination information of the subject. The patient information of the subject is identification information for identifying the subject, and includes, for example, a patient name of the subject, a patient ID, birth date, sex, and ge. The examination information of the subject is identification information for identifying an examination by a capsule-shaped endoscope (an examination for observing the inside of the digestive tract using the capsule-shaped medical apparatus 2 introduced inside the digestive tract) to be performed on the subject, and includes, for example, an examination ID, and examination date.

The displaying apparatus 10 is realized by various displays such as a CRT display and a liquid crystal display, and displays various information which is to be displayed according to the instruction of the control unit 13. Specifically, the displaying apparatus 10 includes position-direction displaying units 10a to 10c which display the position and the direction of the capsule-shaped medical apparatus 2 inside the subject 15, and an image displaying unit 10d which displays in-vivo images of the subject 15 captured by the capsule-shaped medical apparatus 2. The position-direction displaying units 10a to 10c schematically display a position and a direction of the capsule-shaped medical apparatus 2 inside the subject 15 viewed from different directions (for example, directions along X-axis, Y-axis, and Z-axis of the absolute coordinate system of the magnetic guiding apparatus 6). On the other hand, the image displaying unit 10d sequentially displays in real time the in-vivo images of the subject 15 which are sequentially captured by the capsule-shaped medical apparatus 2. Further, the position-direction displaying units 10a to 10c and the image displaying unit 10d of the displaying apparatus 10 may include operation screens to be selected via the selection button group 8c of the operation unit 8 described above. The information displayed on the displaying apparatus 10 includes the patient information, the examination information, and the like of the subject 15 which are useful for the capsule-shaped endoscope examination as well as the in-vivo images of the subject 15 described above.

The direction detecting unit 11 detects a relative direction of the displaying apparatus 10 to the magnetic guiding apparatus 6. Specifically, the direction detecting unit 11 is realized by plural coils and the like whose relative directions are maintained relatively to the displaying apparatus 10. The direction detecting unit 11 detects the magnetic field released by the magnetic guiding apparatus 6 described above. Based on a detection result of the magnetic field, the direction detecting unit 11 detects the relative direction of the displaying apparatus 10 to the absolute coordinate system of the magnetic guiding apparatus 6. The direction detecting unit 11 transmits the detection result of the relative direction of the displaying apparatus 10 to the control unit 13. The relative direction of the displaying apparatus 10 to the magnetic guiding apparatus 6 is used for determining a relative coordinate system of the displaying apparatus 10 to the absolute coordinate system of the magnetic guiding apparatus 6.

The storing unit 12 is realized by various rewritable storage medium such as a RAM, an EFPROM, a flash memory, and a hard disk for storing information. The storing unit 12 stores therein various information which is to be stored according to the instruction of the control unit 13, and outputs information, of the stored various information, which is read out according to the instruction of the control unit 13 to the control unit 13. The storing unit 12 stores therein, under the control of the control unit 13, the in-vivo image group of the subject 15, the patient information and the examination information of the subject 15, the position information and the direction information of the capsule-shaped medical apparatus 2 inside the subject 15, and the like.

The control unit 13 controls operations of each component of the capsule guiding system 1 (the position detecting apparatus 3, the receiving apparatus 4, the body position detecting unit 5, the magnetic guiding apparatus 6, the magnetic guiding power unit 7, the operation unit 8, the input unit 9, the displaying apparatus 10, the direction detecting unit 11, and the storing unit 12), and controls input and output of signals to be transmitted among the components. Specifically, the control unit 13 controls each operation of the receiving apparatus 4, the displaying apparatus 10, the direction detecting unit 11, and the storing unit 12 described above based on the instruction information which is input from the input unit 9. Further, the control unit 13 controls, at predetermined time intervals, the amount of electricity supplied from the drive power unit 3b for the drive-magnetic-field generating unit 3a to thereby control the operation of the drive-magnetic-field generating unit 3a for generating the magnetic field. When the magnetic field is generated by the drive-magnetic-field generating unit 3a (in other words, every time the guiding magnetic field from the capsule-shaped medical apparatus 2 is detected by the magnetic field detecting unit 3c), the control unit 13 controls the position-direction calculating unit 3d to calculate the position and the direction of the capsule-shaped medical apparatus 2 inside the subject 15. The control unit 13 controls the body position detecting unit 5 to detect the body position of the subject 15 at predetermined time intervals. The control unit 13 sequentially obtains a calculation result of the position and the direction of the capsule-shaped medical apparatus 2 calculated by the position-direction calculating unit 3d, sequentially obtains the image signal including the in-vivo images of the subject 15 from the receiving apparatus 4, and sequentially obtains a body position detection result of the subject 15 from the body position detecting unit 5.

Further, the control unit 13 includes a display control unit 13a which controls the displaying apparatus 10, a guiding control unit 13b which controls the magnetic guiding of the capsule-shaped medical apparatus 2 by the magnetic guiding apparatus 6, a coordinate-transformation processing unit 13c which performs coordinate transformation on the operation information input from the operation unit 8, a locus generating unit 13d which calculates a locus of the capsule-shaped medical apparatus 2 inside the subject 15, and an image processing unit 13e which generates the image information such as the in-vivo images of the subject 15.

The display control unit 13a controls the relative coordinate system of the displaying apparatus 10 to the magnetic guiding apparatus 6, and the display operation of the displaying apparatus 10. Specifically, the display control unit 13a obtains a detection result of the direction detecting unit 11, i.e., the relative direction information of the displaying apparatus 10 to the magnetic guiding apparatus 6. Based on the obtained relative direction information, the display control unit 13a determines the relative coordinate system of the displaying apparatus 10 to the absolute coordinate system of the magnetic guiding apparatus 6. Based on the relative coordinate system of the displaying apparatus 10, the display control unit 13a sets the coordinate systems of the position-direction displaying units 10a to 10c of the displaying apparatus 10, respectively. The relative direction of the displaying apparatus 10 is, for example, the relative direction of the display screen of the displaying apparatus 10 to the magnetic guiding apparatus 6.

The display control unit 13a obtains the position information and the direction information of the capsule-shaped medical apparatus 2 calculated by the position-direction calculating unit 3d, and displays the obtained position information and direction information of the capsule-shaped medical apparatus 2 on the position-direction displaying units 10a to 10c of the displaying apparatus 10, respectively. In this case, the display control unit 13a displays the position information and the direction information of the capsule-shaped medical apparatus 2 as image information (a capsule image and a subject image described later) processed by the image processing unit 13e, and locus information of the capsule-shaped medical apparatus 2 generated by the locus generating unit 13d on the position-direction displaying units 10a to 10c. When the display control unit 13a obtains the position information and the direction information of the capsule-shaped medical apparatus 2 from the position-direction calculating unit 3d, the display control unit 13a updates the position information, direction information, and the locus information of the capsule-shaped medical apparatus 2 which are to be displayed on the position-direction displaying units 10a to 10c with the latest information. Further, based on the detection result of the body position detecting unit 5, the display control unit 13a determines whether the body position of the subject 15 is changed. When the body position of the subject 15 is changed, the display control unit 13a changes the display information of the position-direction displaying units 10a to 10c according to the change of body position of the subject 15. On the other hand, the display control unit 13a sequentially obtains the image signal from the receiving apparatus 4, and at the same time, displays the in-vivo image generated by the image processing unit 13e (i.e., the in-vivo image of the subject 15 captured by the capsule-shaped medical apparatus 2) on the image displaying unit 10d.

The guiding control unit 13b controls, based on the operation information which is input from the operation unit 8, the amount of electricity supplied from the magnetic guiding power unit 7 for the magnetic guiding apparatus 6. Thus, the guiding control unit 13b controls the magnetic guiding power unit 7, and thereby controlling the magnetic guiding of the capsule-shaped medical apparatus 2 performed by the magnetic guiding apparatus 6 described above. In this case, the guiding control unit 13b adjusts the coordinate system of the display screen of the displaying apparatus 10 and the coordinate system of the operation direction input from the operation unit 8 to be consistent with each other, and controls, based on the operation information which is transformed into the absolute coordinate system of the magnetic guiding apparatus 6 by the coordinate-transformation processing unit 13c, the magnetic guiding of the capsule-shaped medical apparatus 2 performed by the magnetic guiding apparatus 6. Thus, the movement direction and movement speed of the capsule-shaped medical apparatus 2 being magnetically guided are controlled by the guiding control unit 13b. Further, the guiding control unit 13b determines a correspondence relation between the input operation direction of the operation unit 8 (specifically, the input operation direction of the joysticks 8a, 8b) and the movement direction of the capsule-shaped medical apparatus 2 based on the detection result of the direction detecting unit 11, i.e., based on the relative direction of the displaying apparatus 10 to the magnetic guiding apparatus 6. The guiding control unit 13b changes the correspondence relation between the input operation direction and the movement direction of the capsule-shaped medical apparatus 2 according to change of the relative direction of the displaying apparatus 10 to the magnetic guiding apparatus 6.

Coordinate systems of the screen of the displaying apparatus 10 are the coordinate systems of the position-direction displaying units 10a to 10c and are set by the display control unit 13a based on the detection result of the direction detecting unit 11. The input operation direction of the operation unit 8 is represented by the coordinate system which is set based on the tilted direction of the joysticks 8a, 8b of the operation unit 8. The operation information input from the operation unit 8 is the instruction information for instructing the magnetic guiding of the capsule-shaped medical apparatus 2. Thus, the operation information includes the coordinate information which specifies the movement direction of the capsule-shaped medical apparatus 2 being magnetically guided, and the speed information which specifies the movement speed of the capsule-shaped medical apparatus 2 being magnetically guided.

The coordinate-transformation processing unit 13c transforms the coordinate information which is input from the operation unit 8 into the absolute coordinate system of the magnetic guiding apparatus 6. Specifically, the coordinate-transformation processing unit 13c transforms the coordinate information included in the operation information (more specifically, the coordinate information which specifies the movement direction of the capsule-shaped medical apparatus 2 being magnetically guided) input from the operation unit 8 into the coordinate information of the absolute coordinate system of the magnetic guiding apparatus 6 based on the detection result of the direction detecting unit 11, i.e., based on the relative direction information of the displaying apparatus 10 to the absolute coordinate system of the magnetic guiding apparatus 6. The operation information including the coordinate information on which the coordinate transformation is performed by the coordinate-transformation processing unit 13c is used by the guiding control unit 13b described above for controlling the magnetic guiding of the capsule-shaped medical apparatus 2.

The locus generating unit 13d generates the locus information which shows a movement locus of the capsule-shaped medical apparatus 2 inside the subject 15. Specifically, the locus generating unit 13d continuously obtains the position information of the capsule-shaped medical apparatus 2 which is calculated by the position-direction calculating unit 3d, and generates the locus information of the capsule-shaped medical apparatus 2 based on a group of obtained position information of the capsule-shaped medical apparatus 2. The locus information generated by the locus generating unit 13d is a locus which connects the group of position information (information on plural position coordinates) of the capsule-shaped medical apparatus 2 inside the subject 15 by line segments or the like. The locus information is displayed on the position-direction displaying units 10a to 10c of the displaying apparatus 10 based on the control of the display control unit 13a.

The image processing unit 13e generates various image information displayed on the displaying apparatus 10. Specifically, the image processing unit 13e obtains the image signal from the receiving apparatus 4, and performs a predetermined imaging process on the image signal to generate the in-vivo image of the subject 15 (i.e., the in-vivo image captured by the capsule-shaped medical apparatus 2). In receiving the image signal from the receiving apparatus 4, the image processing unit 13e sequentially generates the in-vivo image based on the obtained image signal. The in-vivo images generated by the image processing unit 13e are sequentially displayed on the image displaying unit 10d under the control of the display control unit 13a.

Further, the image processing unit 13e generates a schematic image (hereinafter, "subject image") which schematically shows the subject 15, and a schematic image (hereinafter, "capsule image") which schematically shows the capsule-shaped medical apparatus 2 as the image information for displaying the position and the direction of the capsule-shaped medical apparatus 2 inside the subject 15. The subject image and the capsule image generated by the image processing unit 13e are displayed (specifically, as an overlapped image) on the position-direction displaying units 10a to 10c under the control of the display control unit 13a, respectively.

Figure 2:
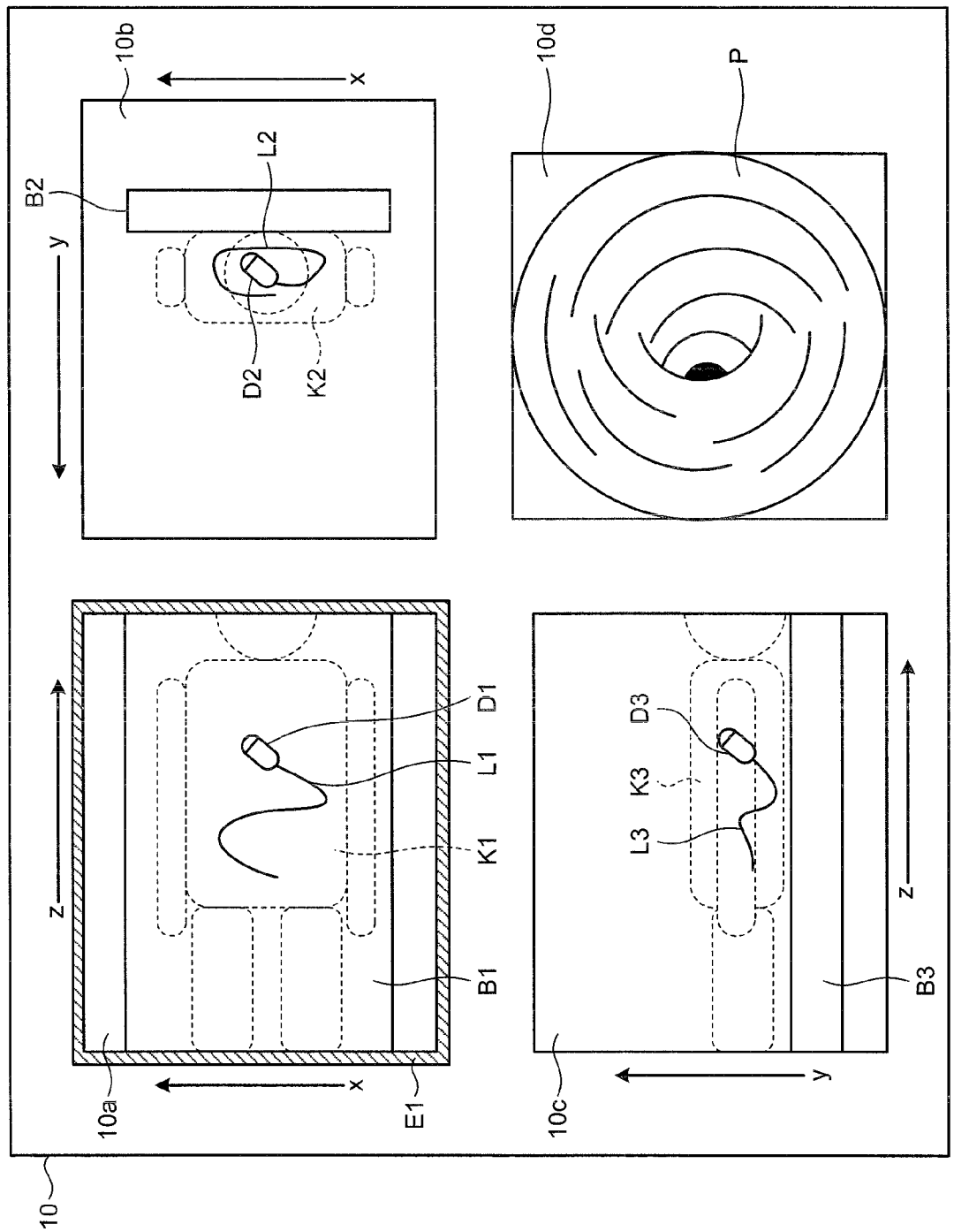
FIG. 2 shows an exemplary schematic configuration of a displaying apparatus of a capsule guiding system according to an embodiment of the present invention.

The displaying apparatus 10 of the capsule guiding system 1 according to the embodiment of the present invention is described in detail. FIG. 2 shows exemplary schematic configuration of the displaying apparatus of the capsule guiding system according to the embodiment of the present invention. The displaying apparatus 10 displays the in-vivo image of the subject 15 captured by the capsule-shaped medical apparatus 2, the position information and the direction information of the capsule-shaped medical apparatus 2 inside the subject 15, and the like under the control of the display control unit 13a.

Specifically, as shown in FIG. 2, the displaying apparatus 10 includes the position-direction displaying units 10a to 10c that display position information, direction information, and the like of the capsule-shaped medical apparatus 2 inside the subject 15, and the image displaying unit 10d that displays an in-vivo image P of the subject 15 captured by the capsule-shaped medical apparatus 2.

The position-direction displaying units 10a to 10c are different-viewpoint displaying units which display the position information and the direction information of the capsule-shaped medical apparatus 2 inside the subject 15 from three different viewpoints. Specifically, the position-direction displaying unit 10a displays the position information and the direction information of the capsule-shaped medical apparatus 2 inside the subject 15, and the like, taking a negative direction of Y-axis of the absolute coordinate system (see FIG. 1) of the magnetic guiding apparatus 6 described above as a viewing direction. Specifically, x-z coordinate system, which is one of the coordinate systems of the display screen of the displaying apparatus 10, is set as the coordinate system of the screen of the position-direction displaying unit 10a, and then the position-direction displaying unit 10a displays a subject image K1 which is a schematic image of the subject 15 viewed from the negative direction of Y-axis of the absolute coordinate system, and a capsule image D1 which is a schematic image of the capsule-shaped medical apparatus 2 viewed from the same direction (the negative direction of Y-axis) as an overlapped image. In the overlapped image, the position-direction displaying unit 10a displays the position information and the direction information (i.e., positional coordinates and a direction vector of the capsule-shaped medical apparatus 2 in X-Z plane of the absolute coordinate system) of the capsule-shaped medical apparatus 2 inside the subject 15, taking a negative direction of the Y-axis as a viewing direction. The direction vector of the capsule-shaped medical apparatus 2 in the X-Z plane is indicated by a longitudinal direction of the capsule image D1. Further, the position-direction displaying unit 10a displays locus information L1 of the capsule-shaped medical apparatus 2 viewed from the negative direction of the Y-axis, and a table image B1 which is a schematic image of the patient table 16 as well as the subject image K1 and the capsule image D1.

The position-direction displaying unit 10a changes a relative position or a relative direction of the subject image K1 and the capsule image D1 under the control of the display control unit 13a according to the magnetic guiding of the capsule-shaped medical apparatus 2 performed by the magnetic guiding apparatus 6. The position-direction displaying unit 10a changes the positions or the directions of the subject image K1, the capsule image D1, and the locus information L1 under the control of the display control unit 13a according to the change of body position of the subject 15. In this case, the position-direction displaying unit 10a fixates the relative positions and the relative directions of the subject image K1, the capsule image D1, and the locus information L1. The position-direction displaying unit 10a changes directions of the subject image K1, the capsule image D1, the locus information L1, and the table image B1 under the control of the display control unit 13a according to change of the relative direction of the displaying apparatus 10 to the magnetic guiding apparatus 6.

The position-direction displaying unit 10b displays the position information and the direction information of the capsule-shaped medical apparatus 2 inside the subject 15, and the like, taking a negative direction of Z-axis of the absolute coordinate system of the magnetic guiding apparatus 6 as a viewing direction. Specifically, x-y coordinate system, which is one of the coordinate systems of the display screen of the displaying apparatus 10, is set as the coordinate system of the screen of the position-direction displaying unit 10b, and then the position-direction displaying unit 10b displays a subject image K2 which is a schematic image of the subject 15 viewed in the negative direction of Z-axis of the absolute coordinate system as a viewing direction, and a capsule image D2 which is a schematic image of the capsule-shaped medical apparatus 2 viewed from the same direction (negative direction of Z-axis) as an overlapped image. In the overlapped image, the position-direction displaying unit 10b displays the position information and the direction information (positional coordinates and a direction vector of the capsule-shaped medical apparatus 2 in X-Y plane of the absolute coordinate system) of the capsule-shaped medical apparatus 2 inside the subject 15 viewed in the negative direction of Z-axis as a viewing direction. The direction vector of the capsule-shaped medical apparatus 2 in the X-Y plane is indicated by the longitudinal direction of the capsule image D2. Further, the position-direction displaying unit 10b displays locus information L2 of the capsule-shaped medical apparatus 2 viewed in the negative direction of the Z-axis as the viewing direction, and a table image B2 which is a schematic image of the patient table 16 as well as the subject image K2 and the capsule image D2.

The position-direction displaying unit 10b changes a relative position or a relative direction of the subject image K2 and the capsule image D2 under the control of the display control unit 13a according to the magnetic guiding of the capsule-shaped medical apparatus 2 performed by the magnetic guiding apparatus 6. The position-direction displaying unit 10b changes the positions or the directions of the subject image K2, the capsule image D2, and the locus information L2 under the control of the display control unit 13a according to the change of the body position of the subject 15. In this case, the position-direction displaying unit 10b fixates the relative positions and the relative directions of the subject image K2, the capsule image D2, and the locus information L2. The position-direction displaying unit 10b changes directions of the subject image K2, the capsule image D2, the locus information L2, and the table image B2 under the control of the display control unit 13a according to the change of relative direction of the displaying apparatus 10 to the magnetic guiding apparatus 6.

The position-direction displaying unit 10c displays the position information and the direction information of the capsule-shaped medical apparatus 2 inside the subject 15, and the like, taking a positive direction of X-axis of the absolute coordinate system of the magnetic guiding apparatus 6 as a viewing direction. Specifically, y-z coordinate system, which is one of the coordinate systems of the display screen of the displaying apparatus 10, is set as the coordinate system of the screen of the position-direction displaying unit 10b, and then the position-direction displaying unit 10c displays a subject image K3 which is a schematic image of the subject 15 viewed in the positive direction of X-axis of the absolute coordinate system as a viewing direction, and a capsule image D3 which is a schematic image of the capsule-shaped medical apparatus 2 viewed from the same direction (positive direction of X-axis) as an overlapped image. In the overlapped image, the position-direction displaying unit 10c displays the position information and the direction information (positional coordinates and a direction vector of the capsule-shaped medical apparatus 2 in Y-Z plane of the absolute coordinate system) of the capsule-shaped medical apparatus 2 inside the subject 15 viewed in the positive direction of X-axis as a viewing direction. The direction vector of the capsule-shaped medical apparatus 2 in the Y-Z plane is indicated by the longitudinal direction of the capsule image D3. Further, the position-direction displaying unit 10c displays locus information L3 of the capsule-shaped medical apparatus 2 viewed in the positive direction of the X-axis as the viewing direction, and a table image B3 which is a schematic image of the patient table 16 as well as the subject image K3 and the capsule image D3.

The position-direction displaying unit 10c changes a relative position or a relative direction of the subject image K3 and the capsule image D3 under the control of the display control unit 13a according to the magnetic guiding of the capsule-shaped medical apparatus 2 performed by the magnetic guiding apparatus 6. The position-direction displaying unit 10c changes the positions or the directions of the subject image K3, the capsule image D3, and the locus information L3 under the control of the display control unit 13a according to the change of the body position of the subject 15. In this case, the position-direction displaying unit 10c fixates the relative positions and the relative directions of the subject image K3, the capsule image D3, and the locus information L3. The position-direction displaying unit 10c changes directions of the subject image K3, the capsule image D3, the locus information L3, and the table image B3 under the control of the display control unit 13a according to the change of relative direction of the displaying apparatus 10 to the magnetic guiding apparatus 6.

When the displaying apparatus 10 is arranged toward the negative direction of X-axis of the absolute coordinate system relative to the magnetic guiding apparatus 6, the viewing direction to view the subject 15 lying on the patient table in the magnetic guiding apparatus 6 substantially coincides with the positive direction of X-axis in the absolute coordinate system of the magnetic guiding apparatus 6. Supposing that the viewpoint (viewing direction from which is the positive direction of X-axis) from which the displaying apparatus 10 views the subject 15 is defined as a standard viewpoint, the position-direction displaying units 10a to 10c shown in FIG.

2 display the position information and the direction information of the capsule-shaped medical apparatus 2 inside the subject 15 viewed from three different viewpoints based on the viewing direction from the standard viewpoint. In this case, x-direction and z-direction of x-z biaxial orthogonal coordinate system set in the position-direction displaying unit 10a coincide with X-direction and Z-direction of the absolute coordinate system of the magnetic guiding apparatus 6, respectively. Similarly, x-direction and y-direction of x-y biaxial orthogonal coordinate system set in the position-direction displaying unit 10b coincide with X-direction and Y-direction of the absolute coordinate system of the magnetic guiding apparatus 6, respectively. Further, y-direction and z-direction of y-z biaxial orthogonal coordinate system set in the position-direction displaying unit 10c coincide with Y-direction and Z-direction of the absolute coordinate system of the magnetic guiding apparatus 6, respectively.

As described above, the position-direction displaying units 10a to 10c change at least the directions of the subject images K1 to K3 and the capsule images D1 to D3 according to the change of relative direction of the displaying apparatus 10 to the magnetic guiding apparatus 6 or the change of body position of the subject 15, so that the body direction of the subject 15 on the patient table 16 viewed from the displaying apparatus 10 can be kept substantially consistent with the body direction of the subject 15 on the display screen (e.g., the subject images K1, K3).

When the viewpoint from which the displaying apparatus 10 views the subject 15 is the standard viewpoint as described above, the directions along axes of each of the coordinate systems of the position-direction displaying units 10a to 10c (x-direction, y-direction, and z-direction) coincide with the directions along axes of the absolute coordinate system of the magnetic guiding apparatus 6 (X-direction, Y-direction, and Z-direction), respectively. On the other hand, when the viewpoint of the displaying apparatus 10 is not the standard viewpoint, x-direction, y-direction, and z-direction of each of the coordinate systems of the position-direction displaying units 10a to 10c are rotated from X-direction, Y-direction, and Z-direction of the absolute coordinate system by the angle formed between the viewing direction of the standard viewpoint and the relative direction of the displaying apparatus 10 to the absolute coordinate system of the magnetic guiding apparatus 6, respectively.

The image displaying unit 10d displays an in-vivo image P of the subject 15 captured by the capsule-shaped medical apparatus 2 under the control of the display control unit 13a. When the control unit 13 receives the image signal of the in-vivo image P from the receiving apparatus 4 (i.e., when the image processing unit 13e generates the in-vivo image P), the image displaying unit 10d sequentially switches the displayed in-vivo image P of the subject 15, and displays the latest in-vivo image P.

Figure 3:
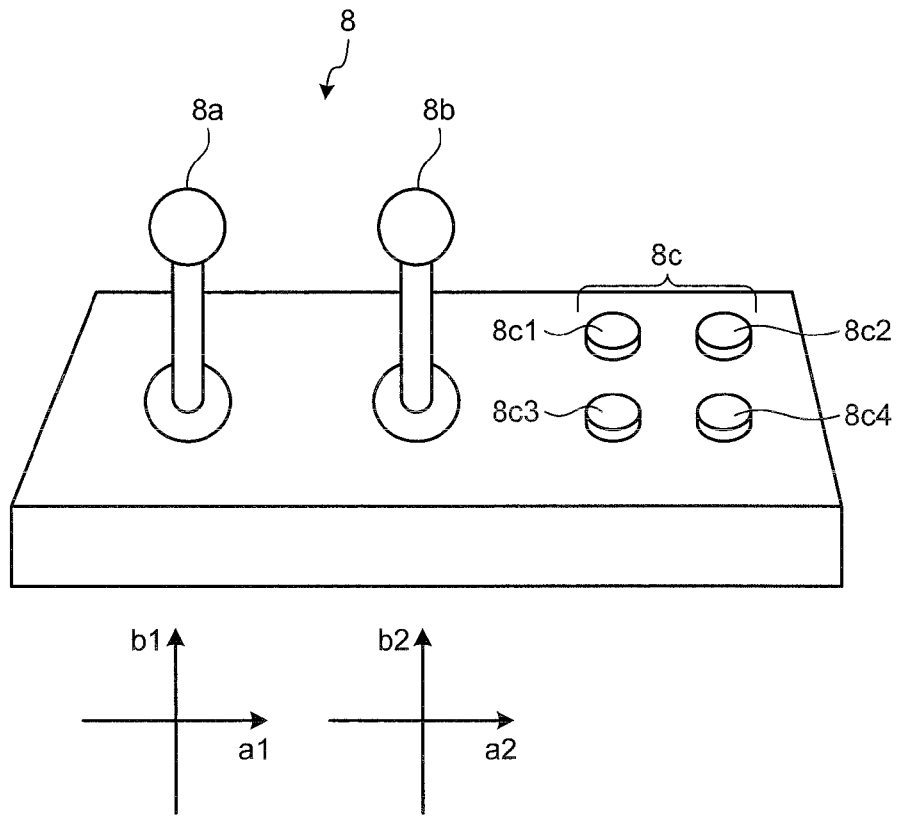
FIG. 3 shows an exemplary schematic configuration of an operation unit of the capsule guiding system according to an embodiment of the present invention.

The operation unit 8 of the capsule guiding system 1 according to the embodiment of the present invention is described in detail. FIG. 3 shows exemplary schematic configuration of the operation unit of the capsule guiding system according to the embodiment. As shown in FIG. 3, the operation unit 8 includes the joysticks 8a, 8b for operating the magnetic guiding of the capsule-shaped medical apparatus 2 by the magnetic guiding apparatus 6, and the selection button group 8c for selecting the operation screen for the magnetic guiding of the capsule-shaped medical apparatus 2 from the display screen of the displaying apparatus 10.

The joysticks 8a, 8b are two input units for inputting the operation information which specifies the movement direction and the movement speed of the capsule-shaped medical apparatus 2 being magnetically guided. Specifically, for the joystick 8a, biaxial orthogonal coordinate system formed by two orthogonal axes (a1-axis, b1-axis) is previously set as the coordinate system of the input operation direction, and the joystick 8a is tilted to a horizontal direction (direction along a1-axis, herein after "a1-direction"), or a vertical direction (direction along b1-axis, hereinafter "b1-direction"), or an oblique direction in the biaxial orthogonal coordinate system, whereby the joystick 8a inputs the operation information of the magnetic guiding of the capsule-shaped medical apparatus 2 to the control unit 13. Similarly, for the joystick 8b, biaxial orthogonal coordinate system formed by two orthogonal axes (a2-axis, b2-axis) is previously set as the coordinate system of the input operation direction, and the joystick 8b is tilted to a horizontal direction (direction along a2-axis, hereinafter "a2-direction"), or a vertical direction (direction along b2-axis, hereinafter "b2-direction"), or an oblique direction in the biaxial orthogonal coordinate system, whereby the joystick 8b inputs the operation information of the magnetic guiding of the capsule-shaped medical apparatus 2 to the control unit 13. A combined value of the couple of coordinate information input through the tilting operation of the two joysticks 8a, 8b is information which specifies the three-dimensional movement direction of the capsule-shaped medical apparatus 2 being magnetically guided. As described above, through the tilting operation of the joysticks 8a, 8b, the operation unit 8 inputs the operation information which specifies the three-dimensional movement direction of the capsule-shaped medical apparatus 2 being magnetically guided to the control unit 13.

The coordinate information in the operation information which is input via the joystick 8a specifies the movement direction of the capsule-shaped medical apparatus 2 being magnetically guided, and is determined corresponding to the input operation direction (tilted direction) of the joystick 8a. A tilted amount of the operation information of the joystick 8a specifies the movement speed of the capsule-shaped medical apparatus 2 being magnetically guided. Similarly, the coordinate information in the operation information which is input via the joystick 8b specifies the movement direction of the capsule-shaped medical apparatus 2 being magnetically guided, and is determined corresponding to the input operation direction (tilted direction) of the joystick 8b. A tilted amount of the operation information of the joystick 8b specifies the movement speed of the capsule-shaped medical apparatus 2 being magnetically guided.

As described, the selection button group 8c is a selection unit for selecting the operation screen for the magnetic guiding of the capsule-shaped medical apparatus 2 from the display screen of the displaying apparatus 10. The selection button group 8c includes four selection buttons 8c1, 8c2, 8c3, 8c4 corresponding to the screens displayed on the displaying apparatus 10, i.e., to the position-direction displaying units 10a to 10c and the image displaying unit 10d, respectively.

The selection button 8c1 is an input button for selecting the position-direction displaying unit 10a from the display screen of the displaying apparatus 10 as the operation screen. When the selection button 8c1 is pushed down, the selection information indicating the position-direction displaying unit 10a is input to the control unit 13. The guiding control unit 13b described above selects the position-direction displaying unit 10a as the operation screen based on the selection information which is input from the selection button 8c1, and adjusts x-z coordinate system of the position-direction displaying unit 10a to be consistent with the biaxial orthogonal coordinate system of the joysticks 8a, 8b. In this case, a positive direction of a1-axis in the biaxial orthogonal coordinate system of the joystick 8a is made consistent with a positive direction of z-axis of the position-direction displaying unit 10a, and a positive direction of b1-axis thereof is made consistent with a positive direction of x-axis of the position-direction displaying unit 10a. Further, the positive direction of a2-axis or b2-axis in the biaxial orthogonal coordinate system of the joystick 8b is made consistent with the negative direction of y-axis which is perpendicular to x-axis and z-axis of the position-direction displaying unit 10a.

The selection button 8c2 is an input button for selecting the position-direction displaying unit 10b from the display screen of the displaying apparatus 10 as the operation screen. When the selection button 8c2 is pushed down, the selection information indicating the position-direction displaying unit 10b is input to the control unit 13. The guiding control unit 13b described above selects the position-direction displaying unit 10b as the operation screen based on the selection information which is input from the selection button 8c2, and adjusts x-y coordinate system of the position-direction displaying unit 10b to be consistent with the biaxial orthogonal coordinate system of the joysticks 8a, 8b. In this case, a positive direction of a1-axis in the biaxial orthogonal coordinate system of the joystick 8a is made consistent with a negative direction of y-axis of the position-direction displaying unit 10b, and a positive direction of b1-axis thereof is made consistent with a positive direction of x-axis of the position-direction displaying unit 10b. Further, the positive direction of a2-axis or b2-axis in the biaxial orthogonal coordinate system of the joystick 8b is made consistent with the negative direction of z-axis which is perpendicular to x-axis and y-axis of the position-direction displaying unit 10b.

The selection button 8c3 is an input button for selecting the position-direction displaying unit 10c from the display screen of the displaying apparatus 10 as the operation screen. When the selection button 8c3 is pushed down, the selection information indicating the position-direction displaying unit 10c is input to the control unit 13. The guiding control unit 13b described above selects the position-direction displaying unit 10c as the operation screen based on the selection information which is input from the selection button 8c3, and adjusts y-z coordinate system of the position-direction displaying unit 10c to be consistent with the biaxial orthogonal coordinate system of the joysticks 8a, 8b. In this case, the positive direction of a1-axis in the biaxial orthogonal coordinate system of the joystick 8a is made consistent with a positive direction of z-axis of the position-direction displaying unit 10c, and the positive direction of b1-axis thereof is made consistent with a positive direction of y-axis of the position-direction displaying unit 10c. Further, the positive direction of a2-axis or b2-axis in the biaxial orthogonal coordinate system of the joystick 8b is made consistent with the positive direction of x-axis which is perpendicular to y-axis and z-axis of the position-direction displaying unit 10c.

The selection button 8c4 is an input button for selecting the image displaying unit 10d from the display screen of the displaying apparatus 10 as the operation screen. When the selection button 8c4 is pushed down, the selection information indicating the image displaying unit 10d is input to the control unit 13. The guiding control unit 13b described above selects the image displaying unit 10d as the operation screen based on the selection information which is input from the selection button 8c4, and adjusts the biaxial orthogonal coordinate system of the image displaying unit 10d to be consistent with the biaxial orthogonal coordinate system of the joysticks 8a, 8b. The biaxial orthogonal coordinate system of the image displaying unit 10d is consistent with a coordinate system defined by a vertical axis and a horizontal axis of a light-receiving surface of an imaging device (described later) embedded in the capsule-shaped medical apparatus 2. In this case, the direction of a1-axis in the biaxial orthogonal coordinate system of the joystick 8a is made consistent with a horizontal direction of the image displaying unit 10d, and the direction of b1-axis thereof is made consistent with a vertical direction of the image displaying unit 10d. Further, the positive direction of a2-axis or b2-axis in the biaxial orthogonal coordinate system of the joystick 8b is made consistent with a direction which vertically crosses the image displaying unit 10d toward a back side of the screen from a front side thereof.

When the operation screen is selected from the display screen of the displaying apparatus 10 through the operation of the selection buttons 8c1, 8c2, 8c3, 8c4, the display control unit 13a described above controls the displaying apparatus 10 to highlight the selected operation screen (one of the position-direction displaying units 10a to 10c and the image displaying unit 10d) on the display screen. Specifically, for example, when the position-direction displaying unit 10a is selected as the operation screen, the displaying apparatus 10 highlights the selected position-direction displaying unit 10a with a marker E1 which is illustrated in FIG. 2 so that operators or the like in an outside can see that the position-direction displaying unit 10a is selected as the operation screen.

Figure 4:
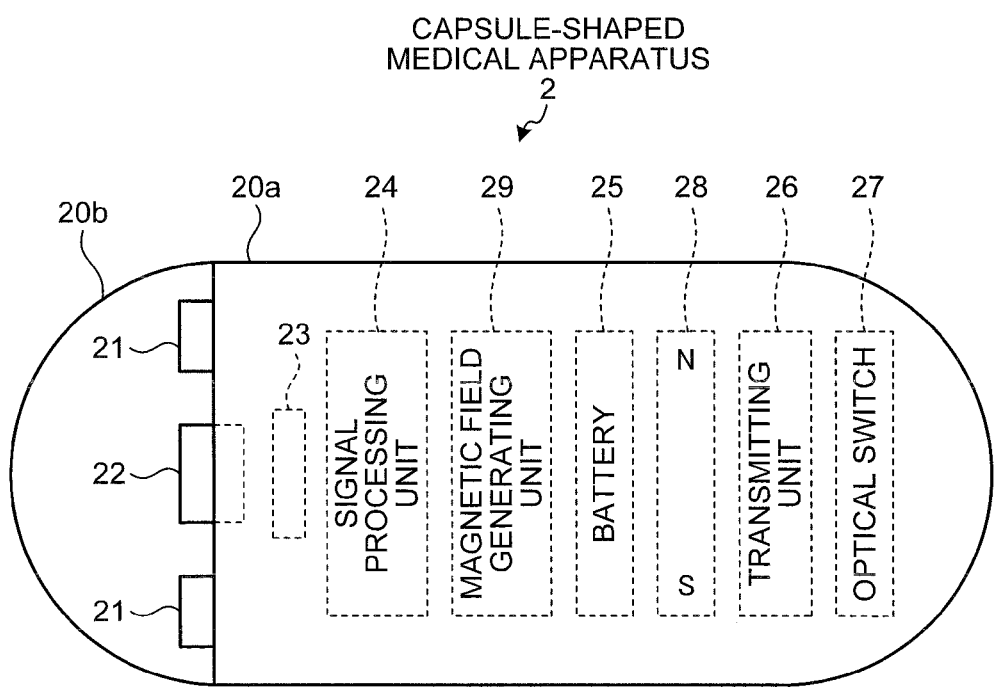
FIG. 4 shows an exemplary schematic configuration of a capsule-shaped medical apparatus of the capsule guiding system according to an embodiment of the present invention.

The capsule-shaped medical apparatus 2 of the capsule guiding system 1 according to the embodiment of the present invention is described in detail. FIG. 4 shows schematic exemplary configuration of the capsule-shaped medical apparatus of the capsule guiding system according to the embodiment of the present invention. As shown in FIG. 4, the capsule-shaped medical apparatus 2 includes a capsule-shaped container formed by a cylinder-shaped container 20a and a dome-shaped container 20b. The whole or a part of the cylinder-shaped container 20a transmits light in a predetermined band of wavelength (e.g., infrared light) while the cylinder-shaped container 20a does not transmit visible light. On the other hand, the dome-shaped container 20b transmits the visible light. One end of the cylinder-shaped container 20a is dome-shaped, and the other end thereof (open end) is sealed by the dome-shaped container 20b, and thereby forming the capsule-shaped container.

The capsule-shaped container formed by the cylinder-shaped container 20a and the dome-shaped container 20b contains, at the side of the dome-shaped container 20b, an illuminating unit 21 which is realized by a LED and the like, a condensing lens 22, and an imaging device 23, to capture a subject around the dome-shaped container 20b. The imaging device 23 performs the capturing in a front direction of the capsule-shaped container, and thus captures the in-vivo image of the subject 15 through the dome-shaped container 20b. The imaging signal which is output from the imaging device 23 is processed by a signal processing unit 24, and is wirelessly transmitted from a transmitting unit 26 to the receiving apparatus 4 described above as the image signal including the in-vivo image of the subject 15.

In the capsule-shaped container, an optical switch 27 which is sensitive to light in a predetermined band of wavelength, e.g., infrared light and a battery 25 are arranged on a side of the cylinder-shaped container 20a. For example, when the optical switch 27 receives infrared light which transmits through a dome-shaped part of the cylinder-shaped container 20a, the optical switch 27 is switched to a power-ON state, and then the battery 25 starts to supply power for each component of the capsule-shaped medical apparatus 2. Once the optical switch 27 receives the infrared light, the optical switch 27 maintains the power-ON state. The optical switch 27 may be switched to a power-OFF state to stop the power supply when the optical switch 27 receives the infrared light again.

In the capsule-shaped container, a magnetic-field generating unit 29 which generates a guiding magnetic field according to a magnetic field of the drive-magnetic-field generating unit 3a is arranged on a side of the cylinder-shaped container 20a. The magnetic-field generating unit 29 is realized, for example, by a coil which is opened along the longitudinal direction of the capsule-shaped container. The magnetic-field generating unit 29 generates a guiding magnetic field due to the magnetic field which is released for detecting the position and the direction of the capsule-shaped medical apparatus 2 in the subject 15 from the drive-magnetic-field generating unit 3a, and outputs the generated guiding magnetic field to the magnetic field detecting unit 3c described above.

In the capsule-shaped container, a magnet 28 is arranged on a side of the cylinder-shaped container 20a (for example, near a middle part of the capsule-shaped medical apparatus 2). As shown in FIG. 4, magnetic poles of the magnet 28 are arranged to be perpendicular to the longitudinal direction of the capsule-shaped medical apparatus 2, and thus arranged along a radial direction of the capsule-shaped container. When the rotating magnetic field is applied to the capsule-shaped medical apparatus 2, the magnet 28 rotates like a rotator of a motor according to the rotating magnetic field. The rotation of the magnet 28 rotates the capsule-shaped medical apparatus 2 around a longitudinal axis or a radial axis which is perpendicular to the longitudinal axis in three dimensions. Further, when the gradient magnetic field is applied to the capsule-shaped medical apparatus 2, the magnet 28 is moved in three dimensions according to the gradient magnetic field. The movement of the magnet 28 moves the capsule-shaped medical apparatus 2 in three dimensions within the coordinate space of the absolute coordinate system of the magnetic guiding apparatus 6 described above.

Of the longitudinal direction of the capsule-shaped container described above, the front direction of the capsule-shaped medical apparatus 2 configured as above is the imaging direction of the imaging device 23, and the rear direction of the capsule-shaped medical apparatus 2 is the opposite direction of the imaging direction of the imaging device 23. Thus, when the capsule-shaped medical apparatus 2 moves forward, the capsule-shaped medical apparatus 2 moves in the imaging direction of the imaging device 23, and when the capsule-shaped medical apparatus 2 moves backward, the capsule-shaped medical apparatus 2 moves in the opposite direction of the imaging direction of the imaging device 23. The vertical direction of the capsule-shaped medical apparatus 2 is consistent with the radial direction of the capsule-shaped container described above, and at the same time, the vertical direction of the light-receiving surface of the imaging device 23. The horizontal direction of the capsule-shaped medical apparatus 2 is consistent with the radial direction of the capsule-shaped container described above and also with the horizontal direction of the light-receiving surface of the imaging device 23.

Figure 5:
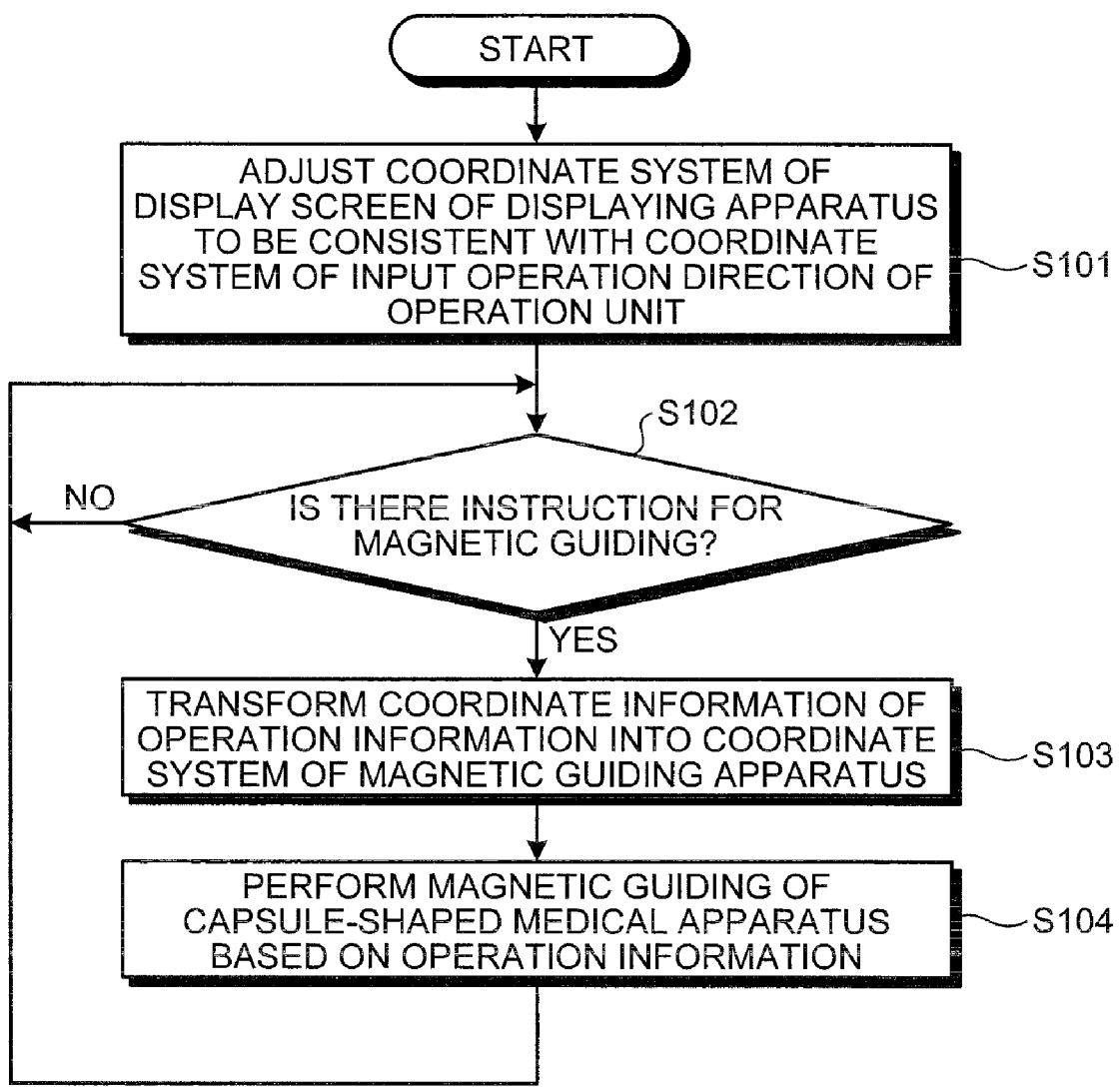
FIG. 5 is a flowchart of a procedure of a control unit for controlling a magnetic guiding apparatus to magnetically guide the capsule-shaped medical apparatus.

A procedure of the control unit 13 for controlling the magnetic guiding of the capsule-shaped medical apparatus 2 performed by the magnetic guiding apparatus 6 is described below. FIG. 5 shows a flowchart of the procedure of the control unit for controlling the magnetic guiding of the capsule-shaped medical apparatus performed by the magnetic guiding apparatus. As shown in FIG. 5, when the control unit 13 controls the magnetic guiding of the capsule-shaped medical apparatus 2 performed by the magnetic guiding apparatus 6, the control unit 13 adjusts the coordinate system of the display screen of the displaying apparatus 10 and the coordinate system of the input operation direction of the operation unit 8 to be consistent with each other (Step S101).

At Step S101, the guiding control unit 13b obtains the detection result of the relative direction of the displaying apparatus 10 to the absolute coordinate system of the magnetic guiding apparatus 6 from the direction detecting unit 11, and determines the relative coordinate system of the position-direction displaying units 10a to 10c to the absolute coordinate system of the magnetic guiding apparatus 6 based on the detection result of the direction detecting unit 11. Specifically, the guiding control unit 13b determines the relative relation between X-Z coordinate system of the absolute coordinate system and x-z coordinate system of the position-direction displaying unit 10a, X-Y coordinate system of the absolute coordinate system and x-y coordinate system of the position-direction displaying unit 10b, and Y-Z coordinate system of the absolute coordinate system and y-z coordinate system of the position-direction displaying unit 10c. After that, the guiding control unit 13b obtains the selection information which is input via the selection button group 8c, selects one of the position-direction displaying units 10a to 10c and the image displaying unit 10d as the operation screen based on the selection information, and adjusts the coordinate system of the selected displaying unit (the coordinate system of one of the position-direction displaying units 10a to 10c and the image displaying unit 10d) and the coordinate system of the input operation direction of the joysticks 8a, 8b to be consistent with each other.

The control unit 13 determines whether there is an instruction for the magnetic guiding of the capsule-shaped medical apparatus 2 (Step S102). When there is no instruction for the magnetic guiding (Step S102, No), the control unit 13 repeats Step S102. At Step S102, when the guiding control unit 13b obtains the operation information for the magnetic guiding of the capsule-shaped medical apparatus 2 which is input from the operation unit 8, the guiding control unit 13b determines that there is an instruction for the magnetic guiding, whereas, when the operation information for the magnetic guiding is not obtained, the guiding control unit 13b determines that there is no instruction for magnetic guiding.

When the control unit 13 determines that there is an instruction for magnetic guiding at Step S102 (Step S102, Yes), the operation information of the magnetic guiding obtained from the operation unit 8 is transformed into the coordinate system of the magnetic guiding apparatus 6, i.e., the absolute coordinate system described above (Step S103).

The operation information of the magnetic guiding of the capsule-shaped medical apparatus 2 includes the coordinate information which is determined by the input operation direction (direction of the tilting operation) of the joysticks 8a, 8b, and the speed information which is determined by the input amount (tilted amount) of the joysticks 8a, 8b. The coordinate information corresponding to the input operation direction is coordinate information of the coordinate system of the displaying unit (i.e., the coordinate system of one of the position-direction displaying units 10a to 10c and the image displaying unit 10d) which was made consistent with the coordinate system of the input operation direction at Step S101. The coordinate information corresponding to the input operation direction specifies the movement direction of the capsule-shaped medical apparatus 2 being magnetically guided. At Step S103, the coordinate-transformation processing unit 13c transforms the coordinate information which specifies the movement direction of the capsule-shaped medical apparatus 2 into the absolute coordinate system of the magnetic guiding apparatus 6. The guiding control unit 13b obtains the operation information (hereinafter, "transformed operation information") which includes the coordinate information which was transformed into the absolute coordinate system and the speed information.

The control unit 13 controls the magnetic guiding of the capsule-shaped medical apparatus 2 based on the transformed operation information which is obtained at Step S103 (Step S104). At Step S104, the guiding control unit 13b combines the coordinate information of the joystick 8a and that of the joystick 8b included in the transformed operation information to determine the three-dimensional movement direction of the capsule-shaped medical apparatus 2 in the absolute coordinate system of the magnetic guiding apparatus 6. The guiding control unit 13b determines the movement speed of the capsule-shaped medical apparatus 2 based on the speed information included in the transformed operation information. The guiding control unit 13b moves the capsule-shaped medical apparatus 2 in three dimensions according to the three-dimensional movement direction and the movement speed determined as above, by controlling the magnetic guiding apparatus 6 so as to magnetically guide the capsule-shaped medical apparatus 2. Through the control of the guiding control unit 13b, the actual movement direction (direction of the magnetic guiding) of the capsule-shaped medical apparatus 2 in the absolute coordinate system of the magnetic guiding apparatus 6 is substantially made consistent with the movement direction of the capsule-shaped medical apparatus 2 being displayed by the displaying apparatus 10 (specifically, the movement direction or the rotation direction of the capsule images D1 to D3 displayed in the position-direction displaying units 10a to 10c).

After that, the control unit 13 returns to Step S102, and repeats Step S102 and subsequent procedures. When the control unit 13 obtains the instruction information for terminating the magnetic guiding which is input from the operation unit 8 or the input unit 9, the control unit 13 terminates the control of the magnetic guiding of the capsule-shaped medical apparatus 2 which is performed by Steps S101 to S104 described above. Further, when the control unit 13 obtains the instruction information for detecting the relative direction of the displaying apparatus 10 to the magnetic guiding apparatus 6 from the input unit 9, the control unit 13 makes the direction detecting unit 11 detect the relative direction of the displaying apparatus 10 to obtain the detection result of the direction detecting unit 11, and repeats Step S101 described above based on the obtained detection result.

Figure 6:
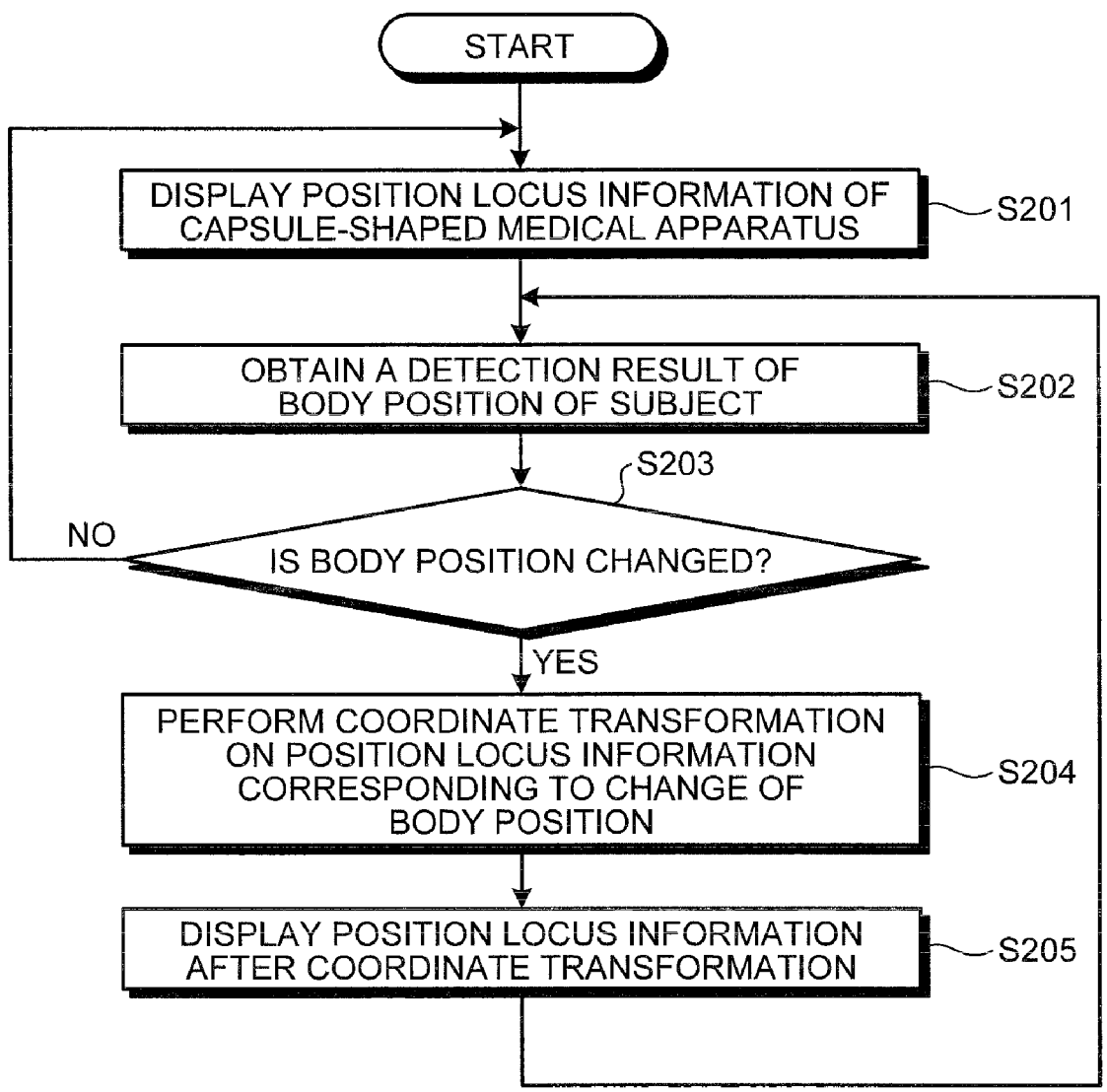
FIG. 6 is a flowchart of a procedure of the control unit for changing display information of a displaying apparatus according to change of a body position of a subject.

A procedure of the control unit 13 for changing the position information and the like of the capsule-shaped medical apparatus 2 which is displayed on the displaying apparatus 10 according to the change of body position of the subject 15 is described. FIG. 6 is a flowchart of the procedure of the control unit for changing the display information of the displaying apparatus according to the change of body position of the subject. As shown in FIG. 6, the control unit 13 makes the displaying apparatus 10 display the position locus information of the capsule-shaped medical apparatus 2 inside the subject 15 (Step S201). The position locus information of the capsule-shaped medical apparatus 2 includes the position information, the direction information, and the locus information of the capsule-shaped medical apparatus 2 in the subject 15. Specifically, the position locus information includes the subject images K1 to K3, the capsule images D1 to D3, and the locus information L1 to L3.

At Step S201, the display control unit 13a obtains the detection result of the relative direction of the displaying apparatus 10 to the absolute coordinate system of the magnetic guiding apparatus 6 from the direction detecting unit 11. Based on the obtained detection result of the direction detecting unit 11, the display control unit 13a determines the directions of the table images B1 to B3 in each of the coordinate systems of the position-direction displaying units 10a to 10c. The display control unit 13a displays the table images B1 to B3 with the determined directions on the position-direction displaying units 10a to 10c, respectively.

Further, at Step S201, the display control unit 13a obtains the detection result of the body position of the subject 15 lying on the patient table 16 from the body position detecting unit 5. Based on the obtained detection result of the body position, the display control unit 13a determines the directions and the body positions of the subject images K1 to K3 in respective coordinate systems of the position-direction displaying units 10a to 10c. The display control unit 13a displays the subject images K1 to K3 with the determined directions and the body positions on the position-direction displaying units 10a to 10c, respectively.

Further, at Step S201, the display control unit 13a obtains the position information and the direction information of the capsule-shaped medical apparatus 2 from the position-direction calculating unit 3d. Based on the obtained position information and the obtained direction information, the display control unit 13a determines the relative position and the relative direction of the capsule image D1 to the subject image K1, the relative position and the relative direction of the capsule image D2 to the subject image K2, and the relative position and the relative direction of the capsule image D3 to the subject image K3. The display control unit 13a displays the capsule images D1 to D3 on the position-direction displaying units 10a to 10c, respectively, in such a manner that the relative relations (the relative positions and the relative directions) between the subject images K1 to K3 and the capsule images D1 to D3 are consistent with the actual relative position and the actual relative direction of the capsule-shaped medical apparatus 2 and the subject 15.

Further, at Step S201, the display control unit 13a displays the locus information of the capsule-shaped medical apparatus 2 which is generated by the locus generating unit 13d described above on the position-direction displaying units 10a to 10c from three different viewpoints. In this case, the display control unit 13a displays the locus information L1 of the capsule-shaped medical apparatus 2 in x-y coordinate system on the position-direction displaying unit 10a, the locus information L2 of the capsule-shaped medical apparatus 2 in x-y coordinate system on the position-direction displaying unit 10b, and the locus information L3 of the capsule-shaped medical apparatus 2 in y-z coordinate system on the position-direction displaying unit 10c.

Then, the control unit 13 obtains the detection result of the current body position of the subject 15 from the body position detecting unit 5 (Step S202), and determines whether the body position of the subject 15 is changed based on the obtained detection result of the body position (Step S203). At Steps S202 and S203, the display control unit 13a obtains from the body position detecting unit 5, the current detection result of the body position of the subject 15 lying on the patient table 16, and checks the difference between the obtained current detection result with the last detection result of the body position to determine whether the body position of the subject 15 is changed. Specifically, the display control unit 13a calculates the variation between the current detection result of the body position, i.e., positional coordinates of each of detection coils 5a to 5c, and the last detection result of the body position, i.e., positional coordinates of each of detection coils 5a to 5c at the time, and compares the calculated variation of the positional coordinates with a previously set threshold value. When the variation of the positional coordinates is equal to or greater than the threshold value, the display control unit 13a determines that the body position of the subject 15 is changed. When the variation of the positional coordinates is smaller than the threshold value, the display control unit 13a determines that the body position of the subject 15 is not changed.

At Step S203, when the control unit 13 determines that the body position of the subject 15 is not changed (Step S203, No), the control unit 13 returns to Step S201 described above, and repeats Step S201 and the subsequent procedures. On the other hand, when the control unit 13 determines that the body position of the subject 15 is changed (Step S203, Yes), the control unit 13 performs the coordinate transformation on the position locus information of the capsule-shaped medical apparatus 2 according to the change of body position of the subject 15 (Step S204), and displays the position locus information after the coordinate transformation on the displaying apparatus 10 (Step S205).

At Steps S204 and S205, the coordinate-transformation processing unit 13c calculates the variation of the coordinates and the direction of the coordinates change between the last detection result and the current detection result of the body position obtained at Step S203, and performs coordinate transformation on the position locus information of the capsule-shaped medical apparatus 2 according to the variation of the coordinates and the direction of the coordinates change calculated above. The display control unit 13a displays the transformed position locus information of the capsule-shaped medical apparatus 2, i.e., the transformed subject images K1 to K3, the transformed capsule images D1 to D3, and the transformed locus information L1 to L3 on the position-direction displaying units 10a to 10c, respectively. As a result, the subject images K1 to K3, the capsule images D1 to D3, and the locus information L1 to L3 are shifted or rotated by the coordinate variation of the coordinate transformation in the direction of the coordinate change with the relative positions and the relative directions to each other being fixated. As described, the display control unit 13a can change the display position and the display direction of the subject images K1 to K3, the capsule images D1 to D3, and the locus information L1 to L3 according to the change of body position of the subject 15.

After that, the control unit 13 returns to Step S202 described above, and repeats Step S202 and the subsequent procedures. When the control unit 13 obtains the instruction information for terminating the displaying process which is input from the input unit 9, the control unit 13 terminates the control of displaying the position locus information of the capsule-shaped medical apparatus 2 which is performed by the procedure through Steps S201 to S205 described above. Further, when the control unit 13 obtains the instruction information for detecting the relative direction of the displaying apparatus 10 to the magnetic guiding apparatus 6 from the input unit 9, the control unit 13 controls the direction detecting unit 11 to detect the relative direction of the displaying apparatus 10 and obtains the detection result from the direction detecting unit 11, and then repeats Step S201 described above based on the obtained detection result.

Figure 7:
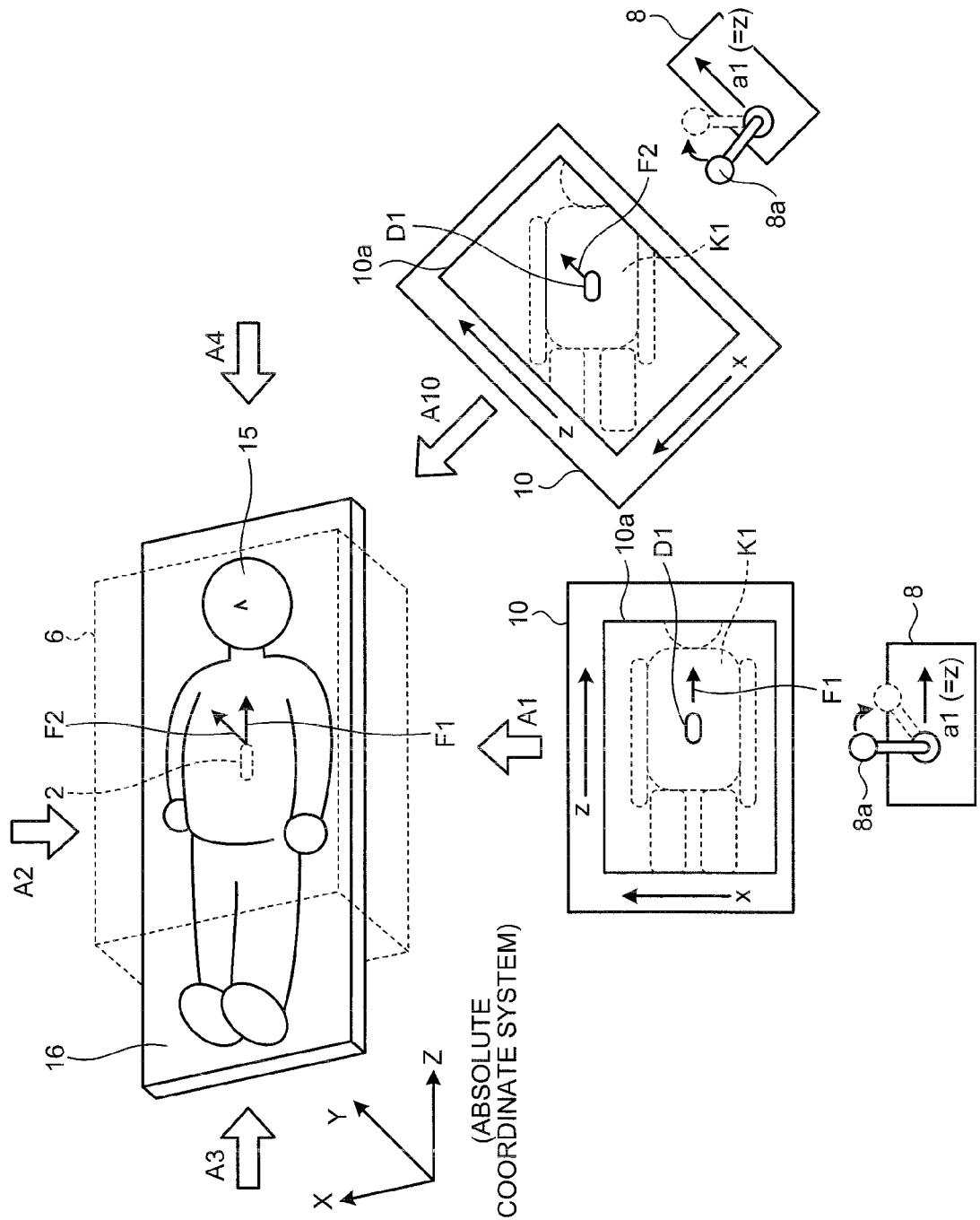
FIG. 7 shows a schematic concrete explanation of operations of the capsule guiding system in operating the magnetic guiding of the capsule-shaped medical apparatus inside the subject.

Specific operations of the capsule guiding system is described below in detail in a case where the position-direction displaying unit 10a is selected from the display screen of the displaying apparatus 10 as the operation screen, and then the joystick 8a is operated with reference to the display information of the position-direction displaying unit 10a to operate the magnetic guiding of the capsule-shaped medical apparatus 2 performed by the magnetic guiding apparatus 6 to thereby magnetically guide the capsule-shaped medical apparatus 2 inside the subject 15. FIG. 7 shows a schematic concrete explanation of the operations of the capsule guiding system in operating the magnetic guiding of the capsule-shaped medical apparatus inside the subject. To make the description concise, FIG. 7 shows only the position-direction displaying unit 10a which is selected as the operation screen in the displaying apparatus 10. FIG. 7 shows only the joystick 8a which is to be operated as the operation unit 8.

As shown in FIG. 7, when the displaying apparatus 10 is arranged toward the negative direction of X-axis of the absolute coordinate system from the magnetic guiding apparatus 6, a viewing direction from the displaying apparatus 10 toward the magnetic guiding apparatus 6, i.e., a viewing direction A1 from the displaying apparatus 10 toward the subject 15 who lies on the patient table 16 is a viewing direction from the standard viewpoint (a positive direction of X-axis) described above.

When the relative direction between the magnetic guiding apparatus 6 and the displaying apparatus 10 is in the above state, the position-direction displaying unit 10a displays, under the control of the display control unit 13a, the subject image K1 in such a manner that the direction of the body of the subject 15 displayed thereon is substantially consistent with the direction of the body of the subject 15 viewed in the viewing direction A1, and further displays the capsule image D1 which overlaps the subject image K1 in such a manner that the relative position and the relative direction between the subject 15 and the capsule-shaped medical apparatus 2 being displayed are consistent with the actual ones. In this case, x-z coordinate system of the position-direction displaying unit 10a is consistent with X-Z coordinate system of the absolute coordinate system of the magnetic guiding apparatus 6. Specifically, the positive and negative directions of z-axis of the position-direction displaying unit 10a are consistent with those of the Z-axis of the absolute coordinate system, and the positive and negative directions of x-axis of the position-direction displaying unit 10a are consistent with those of X-axis of the absolute coordinate system.

The coordinate system of the joystick 8a of the operation unit 8 (biaxial orthogonal coordinate system formed by a1-axis and b1-axis) is made consistent with x-z coordinate system of the position-direction displaying unit 10a which is selected as the operation screen under the control of the guiding control unit 13b described above. Thus, a1-direction of the joystick 8a (horizontal input operation direction) is consistent with z-direction of the position-direction displaying unit 10a (horizontal direction of the display screen), and the b1-direction of the joystick 8a (vertical input operation direction) is consistent with x-direction of the position-direction displaying unit 10a (vertical direction of the display screen).

To move the capsule-shaped medical apparatus 2 inside the subject 15 in the positive direction of Z-axis (a direction F1 shown in FIG. 7) of the absolute coordinate system through the magnetic guiding of the capsule-shaped medical apparatus 2 performed by the magnetic guiding apparatus 6, a user (operator) such as a doctor and a nurse performs a tilting operation which tilts the joystick 8a in the input operation direction which is consistent with the positive direction of z-axis of the position-direction displaying unit 10a which is selected as the operation screen, i.e., in the positive direction of a1-axis. In this case, the joystick 8a inputs the operation information corresponding to the positive direction of a1-axis, which is the tilted direction (in detail, the operation information including coordinate information which specifies the movement direction of the capsule-shaped medical apparatus 2 as the positive direction of z-axis of the position-direction displaying unit 10a), to the control unit 13 described above.

In the control unit 13 which has obtained the operation information, the coordinate-transformation processing unit 13c transforms the coordinate information included in the operation information, i.e., the coordinate information which specifies the movement direction of the capsule-shaped medical apparatus 2 as the positive direction of z-axis of the position-direction displaying unit 10a, into the coordinate information in the absolute coordinate system of the magnetic guiding apparatus 6. Thus, the coordinate information which specifies the movement direction as the positive direction of z-axis is transformed into the coordinate information which specifies the movement direction as the positive direction of Z-axis (the direction F1 shown in FIG. 7) in the absolute coordinate system. The guiding control unit 13b controls the magnetic guiding apparatus 6 based on the operation information including the transformed coordinate information, and thus magnetically guides the capsule-shaped medical apparatus 2 inside the subject 15 in the direction F1.

In the above state of the magnetic guiding, the capsule-shaped medical apparatus 2 inside the subject 15 is moved in the direction F1 according to the magnetic field of the magnetic guiding apparatus 6, and the position-direction displaying unit 10a changes the relative relation between the subject image K1 and the capsule image D1 according to the movement of the capsule-shaped medical apparatus 2 in the direction F1. Specifically, the position-direction displaying unit 10a moves the capsule image D1 in the positive direction of z-axis (i.e., the direction F1 shown in FIG. 7) relatively to the subject image K1. As described above, the capsule guiding system 1 according to the embodiment of the present invention adjusts the coordinate system of the display screen (operation screen) of the displaying apparatus 10 and the coordinate system of the input operation direction of the operation unit 8 to be consistent with each other, and magnetically guides the capsule-shaped medical apparatus 2 in the movement direction corresponding to the input operation direction of the operation unit 8.

On the other hand, as shown in FIG. 7, when the displaying apparatus 10 is arranged obliquely to the magnetic guiding apparatus 6 (e.g., in an oblique direction from Z-axis of the absolute coordinate system), a viewing direction from the displaying apparatus 10 toward the magnetic guiding apparatus 6, i.e., a viewing direction A10 in which the displaying apparatus 10 views the subject 15 who lies on the patient table 16 is oblique to and makes an acute angle with the positive direction of X-axis or the negative direction of Z-axis of the absolute coordinate system.

In the above state of the relative direction between the magnetic guiding apparatus 6 and the displaying apparatus 10, the position-direction displaying unit 10a displays, under the control of the display control unit 13a described above, the subject image K1 in a manner such that the direction of the body of the subject 15 viewed in the viewing direction A10 is substantially consistent with the displayed direction of the body of the subject 15, and displays the capsule image D1 as an overlapped image on the subject image K1 in a manner such that the relative position and the relative direction between the subject 15 and the capsule-shaped medical apparatus 2 being displayed are consistent with the actual ones. In this case, the viewing direction A10 from the displaying apparatus 10 makes a predetermined angle (hereinafter, "viewpoint angle") with the viewing direction of the standard viewpoint described above (i.e., the viewing direction A1 shown in FIG. 7), and the x-z coordinate system of the position-direction displaying unit 10a is consistent with a coordinate system which is rotated around Y-axis by the viewpoint angle from X-Z coordinate system of the absolute coordinate system of the magnetic guiding apparatus 6. Specifically, the positive and negative directions of z-axis of the position-direction displaying unit 10a are consistent with an axis which is rotated around Y-axis by the viewpoint angle from the positive and negative directions of Z-axis of the absolute coordinate system, and the positive and negative directions of x-axis of the position-direction displaying unit 10a are consistent with an axis which is rotated around Y-axis by the viewpoint angle from the positive and negative directions of X-axis of the absolute coordinate system.

Similarly to the above description of the viewing direction of the standard viewpoint (i.e., viewing direction A1), the coordinate system of the joystick 8a of the operation unit 8 is consistent with x-y coordinate system of the position-direction displaying unit 10a which is selected as the operation screen. Specifically, a1-direction of the joystick 8a (horizontal input operation direction) is consistent with z-direction of the position-direction displaying unit 10a (horizontal direction on the display screen), and b1-direction of the joystick 8a (vertical input operation direction) is consistent with x-direction of the position-direction displaying unit 10a (vertical direction on the display screen).

To move the capsule-shaped medical apparatus 2 inside the subject 15 in a direction F2 of the absolute coordinate system through the magnetic guiding of the capsule-shaped medical apparatus 2 performed by the magnetic guiding apparatus 6, the user (operator) such as a doctor and a nurse performs the tilting operation which tilts the joystick 8a in the input operation direction which is consistent with the positive direction of z-axis (i.e., the direction F2 shown in FIG. 7) of the position-direction displaying unit 10a which is selected as the operation screen, i.e., in the positive direction of a1-axis. In this case, the joystick 8a inputs the operation information corresponding to the positive direction of a1-axis, which is the tilted direction, (in detail, the operation information including coordinate information which specifies the movement direction of the capsule-shaped medical apparatus 2 as the positive direction of z-axis of the position-direction displaying unit 10a) to the control unit 13 described above.

In the control unit 13 which has obtained the operation information, the coordinate-transformation processing unit 13c transforms the coordinate information included in the operation information, i.e., the coordinate information which specifies the movement direction of the capsule-shaped medical apparatus 2 as the positive direction of z-axis of the position-direction displaying unit 10a, into the coordinate information in the absolute coordinate system of the magnetic guiding apparatus 6. Thus, the coordinate information which specifies the movement direction as the positive direction of z-axis is transformed into the coordinate information which specifies the movement direction as the direction F2 of the absolute coordinate system. The guiding control unit 13b controls the magnetic guiding apparatus 6 based on the operation information including the transformed coordinate information, and thus magnetically guides the capsule-shaped medical apparatus 2 inside the subject 15 in the direction F2.

In the above state of the magnetic guiding, the capsule-shaped medical apparatus 2 inside the subject 15 is moved in the direction F2 according to the magnetic field of the magnetic guiding apparatus 6, and the position-direction displaying unit 10a changes the relative relation between the subject image K1 and the capsule image D1 according to the movement of the capsule-shaped medical apparatus 2 in the direction F2. Specifically, the position-direction displaying unit 10a moves the capsule image D1 in the positive direction of z-axis (i.e., the direction F2 shown in FIG. 7) relatively to the subject image K1.

As described above, even when the viewing direction from the displaying apparatus 10 toward the subject 15 lying on the patient table 16 differs from the viewing direction from the standard viewpoint, the capsule guiding system 1 according to the embodiment of the present invention adjusts the coordinate system of the display screen (operation screen) of the displaying apparatus 10 and the coordinate system of the input operation direction of the operation unit 8 to be consistent with each other, and magnetically guides the capsule-shaped medical apparatus 2 in the movement direction corresponding to the input operation direction of the operation unit 8. In this case, the guiding control unit 13b changes the relative relation between the input operation direction of the operation unit 8 and the movement direction of the capsule-shaped medical apparatus 2 in the absolute coordinate system according to the relative change of the viewing direction of the displaying apparatus 10 to the viewing direction of the standard viewpoint above, in other words, change in relative direction of the displaying apparatus 10 to the magnetic guiding apparatus 6.

Further, in the capsule guiding system 1 according to the embodiment of the present invention, when the position-direction displaying unit 10b or the position-direction displaying unit 10c is selected from the display screen of the displaying apparatus 10 as the operation screen, the coordinate system of the display screen (operation screen) of the displaying apparatus 10 is made consistent with the coordinate system of the input operation direction of the operation unit 8, and the capsule-shaped medical apparatus 2 is magnetically guided in the movement direction corresponding to the input operation direction of the operation unit 8, similarly to the description of the position-direction displaying unit 10a.

Figure 8:
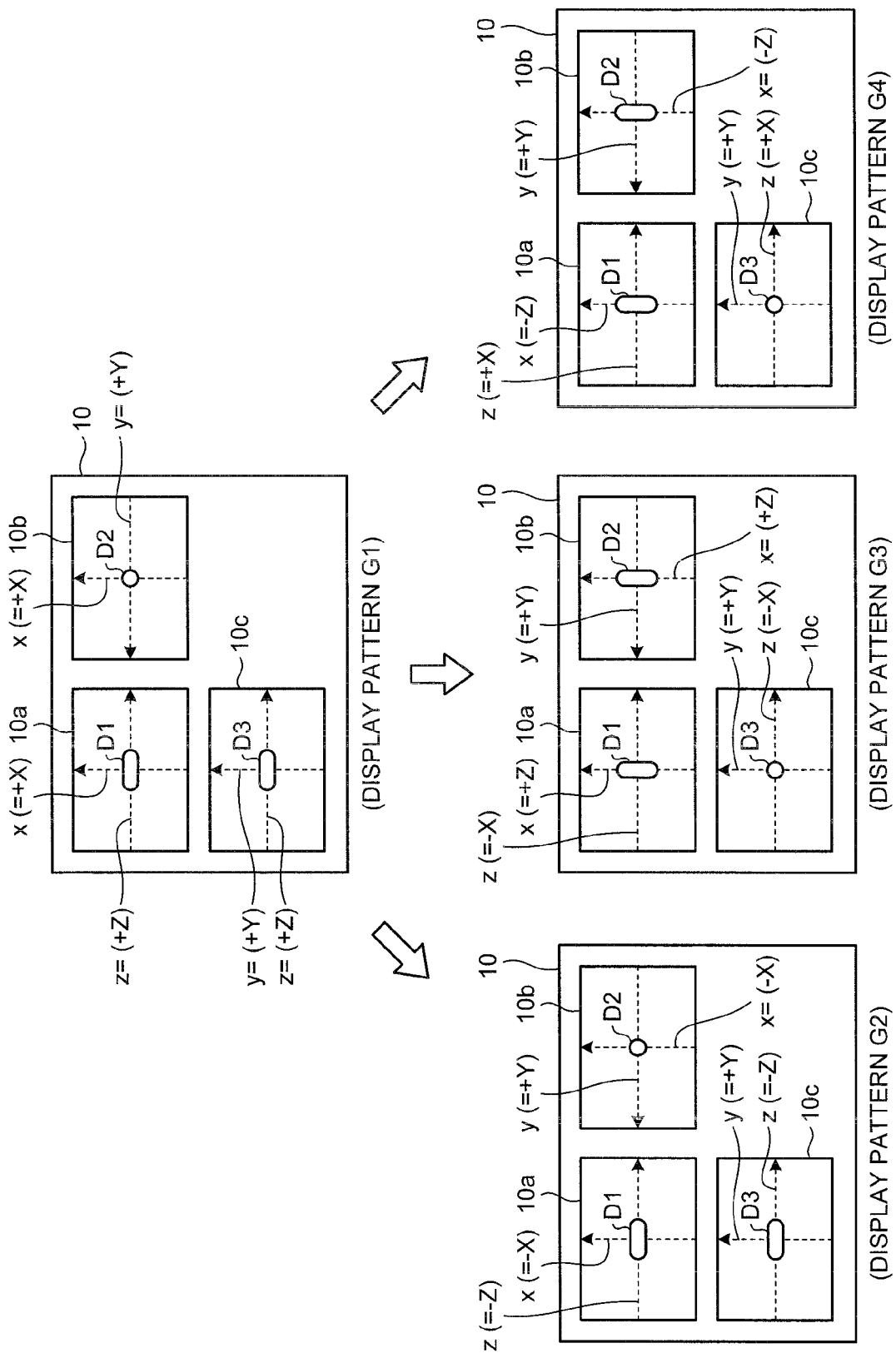
FIG. 8 is a schematic illustration of a correspondence relation between a coordinate system of the magnetic guiding apparatus and a coordinate system of a display screen of a displaying apparatus.

The following describes the correspondence relation between the input operation direction of the operation unit 8 and the movement direction of the capsule-shaped medical apparatus 2 being magnetically guided. The correspondence relation changes according to the change of the relative direction of the displaying apparatus 10 to the magnetic guiding apparatus 6. The following describes a case where a movement operation (moving forward, moving backward, and the like) of the capsule-shaped medical apparatus 2 is performed through the input operation of the joystick 8a of the operation unit 8, and a rotation operation (rotating and the like) of the capsule-shaped medical apparatus 2 is performed through the input operation of the joystick 8b. FIG. 8 is a schematic illustration of the correspondence relation between a coordinate system of the magnetic guiding apparatus and the coordinate system of the display screen of the displaying apparatus. The correspondence relation changes when the relative direction of the displaying apparatus to the magnetic guiding apparatus is changed. FIG. 9 is a schematic illustration of a correspondence relation between the input operation direction of the operation unit and the movement direction of the capsule-shaped medical apparatus. The correspondence relation changes when the relative direction of the displaying apparatus to the magnetic guiding apparatus is changed. For the convenience of description, FIG. 8 shows only the capsule images D1 to D3 as the display information of the position-direction displaying units 10a to 10c, and does not show the image displaying unit 10d.

When the displaying apparatus 10 is arranged toward the negative direction of X-axis of the absolute coordinate system from the magnetic guiding apparatus 6, and thus the viewing direction from the displaying apparatus 10 to the subject 15 lying on the patient table 16 is the viewing direction from the standard viewpoint (the viewing direction A1 shown in FIG. 7), the displaying apparatus 10 displays the capsule images D1 to D3 on the position-direction displaying units 10a to 10c, respectively, in a manner such that the displaying apparatus 10 displays the capsule-shaped medical apparatus 2 inside the subject 15 from three different viewpoints based on the viewing direction A1 as shown in a display pattern G1 in FIG. 8. In the display pattern G1, the positive direction of x-axis of x-z coordinate system of the position-direction displaying unit 10a is consistent with the positive direction of X-axis of the absolute coordinate system of the magnetic guiding apparatus 6, and the positive direction of z-axis of x-z coordinate system thereof is consistent with the positive direction of Z-axis of the absolute coordinate system of the magnetic guiding apparatus 6. The positive direction of x-axis of x-y coordinate system of the position-direction displaying unit 10b is consistent with the positive direction of X-axis of the absolute coordinate system of the magnetic guiding apparatus 6, and the positive direction of y-axis of x-y coordinate system is consistent with the positive direction of Y-axis of the absolute coordinate system. The positive direction of y-axis of y-z coordinate system of the position-direction displaying unit 10c is consistent with the positive direction of Y-axis of the absolute coordinate system of the magnetic guiding apparatus 6, and the positive direction of z-axis of y-z coordinate system is consistent with the positive direction of Z-axis of the absolute coordinate system.

When the position-direction displaying unit 10a is selected as the operation screen of the magnetic guiding of the capsule-shaped medical apparatus 2, the guiding control unit 13b adjusts x-z coordinate system of the position-direction displaying unit 10a and each of the coordinate systems of joysticks 8a, 8b of the operation unit 8 to be consistent with each other. Specifically, the guiding control unit 13b adjusts the positive direction of x-axis of the position-direction displaying unit 10a and each of the positive directions of b1-axis and b2-axis of the joysticks 8a, 8b to be consistent with each other, and adjusts the positive direction of z-axis of the position-direction displaying unit 10a and each of the positive directions of a1-axis and a2-axis of the joysticks 8a, 8b to be consistent with each other. In this case, the guiding control unit 13b determines the correspondence relation between the input operation direction of the joysticks 8a, 8b of the operation unit 8 and the movement direction of the capsule-shaped medical apparatus 2 being magnetically guided as shown in an operation pattern H1 in FIG. 9.

Specifically, the guiding control unit 13b moves the capsule-shaped medical apparatus 2 in the positive direction of X-axis of the absolute coordinate system based on the operation information which is input when the joystick 8a is tilted in the positive direction of b1-axis, and moves the capsule-shaped medical apparatus 2 in the negative direction of X-axis of the absolute coordinate system based on the operation information which is input when the joystick 8a is tilted in the negative direction of b1-axis. On the other hand, the guiding control unit 13b moves the capsule-shaped medical apparatus 2 in the positive direction of Z-axis of the absolute coordinate system based on the operation information which is input when the joystick 8a is tilted in the positive direction of a1-axis, and moves the capsule-shaped medical apparatus 2 in the negative direction of Z-axis of the absolute coordinate system based on the operation information which is input when the joystick 8a is tilted in the negative direction of a1-axis.

Further, the guiding control unit 13b rotates the capsule-shaped medical apparatus 2 around Z-axis of the absolute coordinate system (i.e., in the direction from the positive direction of Y-axis to the positive direction of X-axis) based on the operation information which is input when the joystick 8b is tilted in the positive direction of b2-axis, and rotates the capsule-shaped medical apparatus 2 around Z-axis of the absolute coordinate system (i.e., in the direction from the positive direction of Y-axis to the negative direction of X-axis) based on the operation information which is input when the joystick 8b is tilted in the negative direction of b2-axis. On the other hand, the guiding control unit 13b rotates the capsule-shaped medical apparatus 2 around X-axis of the absolute coordinate system (i.e., in the direction from the positive direction of Y-axis to the positive direction of Z-axis) based on the operation information which is input when the joystick 8b is tilted in the positive direction of a2-axis, and rotates the capsule-shaped medical apparatus 2 around X-axis of the absolute coordinate system (i.e., in the direction from the positive direction of Y-axis to the negative direction of Z-axis) based on the operation information which is input when the joystick 8b is tilted in the negative direction of a2-axis.

On the other hand, when the displaying apparatus 10 is arranged toward the positive direction of X-axis of the absolute coordinate system from the magnetic guiding apparatus 6, and thus the viewing direction from the displaying apparatus 10 to the subject 15 lying on the patient table 16 is the negative direction of X-axis (viewing direction A2), the displaying apparatus 10 displays the capsule images D1 to D3 on the position-direction displaying units 10a to 10c, respectively, in a manner such that the displaying apparatus 10 displays the capsule-shaped medical apparatus 2 inside the subject 15 from three different viewpoints based on the viewing direction A2 as shown in a display pattern G2 in FIG. 8. In the display pattern G2, the positive direction of x-axis of x-z coordinate system of the position-direction displaying unit 10a is consistent with the negative direction of X-axis of the absolute coordinate system of the magnetic guiding apparatus 6, and the positive direction of z-axis of x-z coordinate system thereof is consistent with the negative direction of Z-axis of the absolute coordinate system of the magnetic guiding apparatus 6. The positive direction of x-axis of x-y coordinate system of the position-direction displaying unit 10b is consistent with the negative direction of X-axis of the absolute coordinate system of the magnetic guiding apparatus 6, and the positive direction of y-axis of x-y coordinate system is consistent with the positive direction of Y-axis of the absolute coordinate system. The positive direction of y-axis of y-z coordinate system of the position-direction displaying unit 10c is consistent with the positive direction of Y-axis of the absolute coordinate system of the magnetic guiding apparatus 6, and the positive direction of z-axis of y-z coordinate system is consistent with the negative direction of Z-axis of the absolute coordinate system.

When the position-direction displaying unit 10a is selected as the operation screen of the magnetic guiding of the capsule-shaped medical apparatus 2, the guiding control unit 13b adjusts x-z coordinate system of the position-direction displaying unit 10a and each of the coordinate systems of joysticks 8a, 8b of the operation unit 8 to be consistent with each other. Specifically, the guiding control unit 13b adjusts the positive direction of x-axis of the position-direction displaying unit 10a and each of the positive directions of b1-axis and b2-axis of the joysticks 8a, 8b to be consistent with each other, and adjusts the positive direction of z-axis of the position-direction displaying unit 10a and each of the positive directions of a1-axis and a2-axis of the joysticks 8a, 8b to be consistent with each other. In this case, the guiding control unit 13b determines the correspondence relation between the input operation direction of the joysticks 8a, 8b of the operation unit 8 and the movement direction of the capsule-shaped medical apparatus 2 being magnetically guided as shown in an operation pattern H2 in FIG. 9.

Specifically, the guiding control unit 13b moves the capsule-shaped medical apparatus 2 in the negative direction of X-axis of the absolute coordinate system based on the operation information which is input when the joystick 8a is tilted in the positive direction of b1-axis, and moves the capsule-shaped medical apparatus 2 in the positive direction of X-axis of the absolute coordinate system based on the operation information which is input when the joystick 8a is tilted in the negative direction of b1-axis. On the other hand, the guiding control unit 13b moves the capsule-shaped medical apparatus 2 in the negative direction of Z-axis of the absolute coordinate system based on the operation information which is input when the joystick 8a is tilted in the positive direction of a1-axis, and moves the capsule-shaped medical apparatus 2 in the positive direction of Z-axis of the absolute coordinate system based on the operation information which is input when the joystick 8a is tilted in the negative direction of a1-axis.

Further, the guiding control unit 13b rotates the capsule-shaped medical apparatus 2 around Z-axis of the absolute coordinate system (i.e., in the direction from the positive direction of Y-axis to the negative direction of X-axis) based on the operation information which is input when the joystick 8b is tilted in the positive direction of b2-axis, and rotates the capsule-shaped medical apparatus 2 around Z-axis of the absolute coordinate system (i.e., in the direction from the positive direction of Y-axis to the positive direction of X-axis) based on the operation information which is input when the joystick 8b is tilted in the negative direction of b2-axis. On the other hand, the guiding control unit 13b rotates the capsule-shaped medical apparatus 2 around X-axis of the absolute coordinate system (i.e., in the direction from the positive direction of Y-axis to the negative direction of Z-axis) based on the operation information which is input when the joystick 8b is tilted in the positive direction of a2-axis, and rotates the capsule-shaped medical apparatus 2 around X-axis of the absolute coordinate system (i.e., in the direction from the positive direction of Y-axis to the positive direction of Z-axis) based on the operation information which is input when the joystick 8b is tilted in the negative direction of a2-axis.

On the other hand, when the displaying apparatus 10 is arranged toward the negative direction of Z-axis of the absolute coordinate system from the magnetic guiding apparatus 6, and thus the viewing direction from the displaying apparatus 10 to the subject 15 lying on the patient table 16 is the positive direction of Z-axis (viewing direction A3), the displaying apparatus 10 displays the capsule images D1 to D3 on the position-direction displaying units 10a to 10c, respectively, in a manner such that the displaying apparatus 10 displays the capsule-shaped medical apparatus 2 inside the subject 15 from three different viewpoints based on the viewing direction A3 as shown in a display pattern G3 in FIG. 8. In the display pattern G3, the positive direction of x-axis of x-z coordinate system of the position-direction displaying unit 10a is consistent with the positive direction of Z-axis of the absolute coordinate system of the magnetic guiding apparatus 6, and the positive direction of z-axis of x-z coordinate system thereof is consistent with the negative direction of X-axis of the absolute coordinate system of the magnetic guiding apparatus 6. The positive direction of x-axis of x-y coordinate system of the position-direction displaying unit 10b is consistent with the positive direction of Z-axis of the absolute coordinate system of the magnetic guiding apparatus 6, and the positive direction of y-axis of x-y coordinate system is consistent with the positive direction of Y-axis of the absolute coordinate system. The positive direction of y-axis of y-z coordinate system of the position-direction displaying unit 10c is consistent with the positive direction of Y-axis of the absolute coordinate system of the magnetic guiding apparatus 6, and the positive direction of z-axis of y-z coordinate system is consistent with the negative direction of X-axis of the absolute coordinate system.

When the position-direction displaying unit 10a is selected as the operation screen of the magnetic guiding of the capsule-shaped medical apparatus 2, the guiding control unit 13b adjusts x-z coordinate system of the position-direction displaying unit 10a and each of the coordinate systems of the joysticks 8a, 8b of the operation unit 8 to be consistent with each other. Specifically, the guiding control unit 13b adjusts the positive direction of x-axis of the position-direction displaying unit 10a and each of the positive directions of b1-axis and b2-axis of the joysticks 8a, 8b to be consistent with each other, and adjusts the positive direction of z-axis of the position-direction displaying unit 10a and each of the positive directions of a1-axis and a2-axis of the joysticks 8a, 8b to be consistent with each other. In this case, the guiding control unit 13b determines the correspondence relation between the input operation direction of the joysticks 8a, 8b of the operation unit 8 and the movement direction of the capsule-shaped medical apparatus 2 being magnetically guided as shown in an operation pattern H3 in FIG. 9.

Specifically, the guiding control unit 13b moves the capsule-shaped medical apparatus 2 in the positive direction of Z-axis of the absolute coordinate system based on the operation information which is input when the joystick 8a is tilted in the positive direction of b1-axis, and moves the capsule-shaped medical apparatus 2 in the negative direction of Z-axis of the absolute coordinate system based on the operation information which is input when the joystick 8a is tilted in the negative direction of b1-axis. On the other hand, the guiding control unit 13b moves the capsule-shaped medical apparatus 2 in the negative direction of X-axis of the absolute coordinate system based on the operation information which is input when the joystick 8a is tilted in the positive direction of a1-axis, and moves the capsule-shaped medical apparatus 2 in the positive direction of X-axis of the absolute coordinate system based on the operation information which is input when the joystick 8a is tilted in the negative direction of a1-axis.

Further, the guiding control unit 13b rotates the capsule-shaped medical apparatus 2 around X-axis of the absolute coordinate system (i.e., in the direction from the positive direction of Y-axis to the positive direction of Z-axis) based on the operation information which is input when the joystick 8b is tilted in the positive direction of b2-axis, and rotates the capsule-shaped medical apparatus 2 around X-axis of the absolute coordinate system (i.e., in the direction from the positive direction of Y-axis to the negative direction of Z-axis) based on the operation information which is input when the joystick 8b is tilted in the negative direction of b2-axis. On the other hand, the guiding control unit 13b rotates the capsule-shaped medical apparatus 2 around Z-axis of the absolute coordinate system (i.e., in the direction from the positive direction of Y-axis to the negative direction of X-axis) based on the operation information which is input when the joystick 8b is tilted in the positive direction of a2-axis, and rotates the capsule-shaped medical apparatus 2 around Z-axis of the absolute coordinate system (i.e., in the direction from the positive direction of Y-axis to the positive direction of X-axis) based on the operation information which is input when the joystick 8b is tilted in the negative direction of a2-axis.

On the other hand, when the displaying apparatus 10 is arranged toward the positive direction of Z-axis of the absolute coordinate system from the magnetic guiding apparatus 6, and thus the viewing direction from the displaying apparatus 10 to the subject 15 lying on the patient table 16 is the negative direction of Z-axis (viewing direction A4), the displaying apparatus 10 displays the capsule images D1 to D3 on the position-direction displaying units 10a to 10c, respectively, in a manner such that the displaying apparatus 10 displays the capsule-shaped medical apparatus 2 inside the subject 15 from three different viewpoints based on the viewing direction A4 as shown in a display pattern G4 in FIG. 8. In the display pattern G4, the positive direction of x-axis of x-z coordinate system of the position-direction displaying unit 10a is consistent with the negative direction of Z-axis of the absolute coordinate system of the magnetic guiding apparatus 6, and the positive direction of z-axis of x-z coordinate system thereof is consistent with the positive direction of X-axis of the absolute coordinate system of the magnetic guiding apparatus 6. The positive direction of x-axis of x-y coordinate system of the position-direction displaying unit 10b is consistent with the negative direction of Z-axis of the absolute coordinate system of the magnetic guiding apparatus 6, and the positive direction of y-axis of x-y coordinate system is consistent with the positive direction of Y-axis of the absolute coordinate system. The positive direction of y-axis of y-z coordinate system of the position-direction displaying unit 10c is consistent with the positive direction of Y-axis of the absolute coordinate system of the magnetic guiding apparatus 6, and the positive direction of z-axis of y-z coordinate system is consistent with the positive direction of X-axis of the absolute coordinate system.

When the position-direction displaying unit 10a is selected as the operation screen of the magnetic guiding of the capsule-shaped medical apparatus 2, the guiding control unit 13b adjusts x-z coordinate system of the position-direction displaying unit 10a and each of the coordinate systems of the joysticks 8a, 8b of the operation unit 8 to be consistent with each other. Specifically, the guiding control unit 13b adjusts the positive direction of x-axis of the position-direction displaying unit 10a and each of the positive directions of b1-axis and b2-axis of the joysticks 8a, 8b to be consistent with each other, and adjusts the positive direction of z-axis of the position-direction displaying unit 10a and each of the positive directions of a1-axis and a2-axis of the joysticks 8a, 8b to be consistent with each other. In this case, the guiding control unit 13b determines the correspondence relation between the input operation direction of the joysticks 8a, 8b of the operation unit 8 and the movement direction of the capsule-shaped medical apparatus 2 being magnetically guided as shown in an operation pattern H4 in FIG. 9.

Specifically, the guiding control unit 13b moves the capsule-shaped medical apparatus 2 in the negative direction of Z-axis of the absolute coordinate system based on the operation information which is input when the joystick 8a is tilted in the positive direction of b1-axis, and moves the capsule-shaped medical apparatus 2 in the positive direction of Z-axis of the absolute coordinate system based on the operation information which is input when the joystick 8a is tilted in the negative direction of b1-axis. On the other hand, the guiding control unit 13b moves the capsule-shaped medical apparatus 2 in the positive direction of X-axis of the absolute coordinate system based on the operation information which is input when the joystick 8a is tilted in the positive direction of a1-axis, and moves the capsule-shaped medical apparatus 2 in the negative direction of X-axis of the absolute coordinate system based on the operation information which is input when the joystick 8a is tilted in the negative direction of a1-axis.

Further, the guiding control unit 13b rotates the capsule-shaped medical apparatus 2 around X-axis of the absolute coordinate system (i.e., in the direction from the positive direction of Y-axis to the negative direction of Z-axis) based on the operation information which is input when the joystick 8b is tilted in the positive direction of b2-axis, and rotates the capsule-shaped medical apparatus 2 around X-axis of the absolute coordinate system (i.e., in the direction from the positive direction of Y-axis to the positive direction of Z-axis) based on the operation information which is input when the joystick 8b is tilted in the negative direction of b2-axis. On the other hand, the guiding control unit 13b rotates the capsule-shaped medical apparatus 2 around Z-axis of the absolute coordinate system (i.e., in the direction from the positive direction of Y-axis to the positive direction of X-axis) based on the operation information which is input when the joystick 8b is tilted in the positive direction of a2-axis, and rotates the capsule-shaped medical apparatus 2 around Z-axis of the absolute coordinate system (i.e., in the direction from the positive direction of Y-axis to the negative direction of X-axis) based on the operation information which is input when the joystick 8b is tilted in the negative direction of a2-axis.

The capsule guiding system 1 according to the embodiment of the present invention selects arbitrarily the operation screen for the magnetic guiding from the display screen of the displaying apparatus 10 (i.e., the position-direction displaying units 10a to 10c, and the image displaying unit 10d). The capsule guiding system 1 adjusts the coordinate system of the displaying unit (one of the position-direction displaying units 10a to 10c and the image displaying unit 10d) which is selected as the operation screen and the coordinate system of the input operation direction of the joysticks 8a, 8b to be consistent with each other, and determines the correspondence relation between the input operation direction of the joysticks 8a, 8b and the movement direction of the capsule-shaped medical apparatus 2 being magnetically guided, similarly to the above description of the position-direction displaying unit 10a. Thus, the capsule guiding system 1 can make the capsule-shaped medical apparatus 2 perform the three-dimensional operations (movement and rotation) in the absolute coordinate system of the magnetic guiding apparatus 6 to thereby magnetically guide the capsule-shaped medical apparatus 2.

The following describes the way the display information of the displaying apparatus 10 is changed according to change of the body position of the subject 15 in a case where the subject 15 containing the capsule-shaped medical apparatus 2 inside his body changes his body position from a supine position into a right lateral position on the patient table 16. FIG. 10 shows a schematic concrete explanation of the change of the displaying information of the displaying apparatus according to change in the body position of the subject.

When a viewing direction from the displaying apparatus 10 toward the subject 15 lying on the patient table 16 is the viewing direction from the standard viewpoint described above (see the viewing direction A1 shown in FIG. 7), the displaying apparatus 10 displays the position locus information of the capsule-shaped medical apparatus 2 inside the subject 15 from three viewpoints based on the standard viewpoint as shown in a display pattern G10 of FIG. 10. The position-direction displaying unit 10a displays as an overlapped image the subject image K1 in which the subject 15 lying on the patient table 16 in the supine position is viewed from Y-direction of the absolute coordinate system, the capsule image D1 and the locus information L1 in which the capsule-shaped medical apparatus 2 is viewed from Y-direction, and the table image B1 in which the patient table 16 is viewed from Y-direction. The position-direction displaying unit 10b displays as the overlapped image the subject image K2 in which the subject 15 in the supine position is viewed from Z-direction of the absolute coordinate system, the capsule image D2 and the locus information L2 in which the capsule-shaped medical apparatus 2 is viewed from Z-direction, and the table image B2 in which the patient table 16 is viewed from Z-direction. The position-direction displaying unit 10c displays as the overlapped image the subject image K3 in which the subject 15 in the supine position is viewed from X-direction of the absolute coordinate system, the capsule image D3 and the locus information L3 in which the capsule-shaped medical apparatus 2 is viewed from X-direction, and the table image B3 in which the patient table 16 is viewed from X-direction.

The image displaying unit 10d displays the in-vivo image P of the subject 15 which is captured by the capsule-shaped medical apparatus 2 regardless of the body position of the subject 15 and the viewing direction of the displaying apparatus 10. In this case, the image displaying unit 10d displays the in-vivo image P sequentially in a manner such that the vertical and horizontal directions of the display screen of the displaying apparatus 10 are consistent with those of the in-vivo image P.

When the subject 15 lying on the patient table 16 changes his body position from the supine position into the right lateral position as shown in FIG. 10, the display control unit 13a transforms the display information of the position-direction displaying units 10a to 10c based on the detection result of the body position from the body position detecting unit 5 as described above. Specifically, the coordinate-transformation processing unit 13c calculates the coordinate variation and the direction of the coordinate variation in the detection result of the body position of the subject 15 whose body position changes from the supine position into the right lateral position, and performs the coordinate transformation process on each coordinate information of the subject images K1 to K3, the capsule images D1 to D3, and the locus information L1 to L3 based on the coordinate variation and the direction of the coordinate variation calculated. The display control unit 13a displays the subject images K1 to K3, the capsule images D1 to D3, and the locus information L1 to L3 whose coordinate information is transformed through the coordinate transformation of the coordinate-transformation processing unit 13c on the position-direction displaying units 10a to 10c, respectively.

As shown in FIG. 10, the displaying apparatus 10 performs movement, rotation, and the like on the subject images K1 to K3, the capsule images D1 to D3, and the locus information L1 to L3 according to the change of the body position of the subject 15 under the control of the display control unit 13a. Specifically, as shown in a display pattern G11 in FIG. 10, the position-direction displaying unit 10a maintains the relative position and the relative direction of the subject image K1, the capsule image D1, and the locus information L1, and moves or rotates the subject image K1, the capsule image D1, and the locus information L1 according to the change of body position of the subject 15. The position-direction displaying unit 10b maintains the relative position and the relative direction of the subject image K2, the capsule image D2, and the locus information L2, and moves or rotates the subject image K2, the capsule image D2, and the locus information L2 according to the change of body position of the subject 15. The position-direction displaying unit 10c maintains the relative position and the relative direction of the subject image K3, the capsule image D3, and the locus information L3, and moves or rotates the subject image K3, the capsule image D3, and the locus information L3 according to the change of body position of the subject 15.

The displaying apparatus 10 changes the subject images K1 to K3, the capsule images D1 to D3, and the locus information L1 to L3 according to the change of body position of the subject 15, whereby the actual body direction of the subject 15 viewed in a viewing direction from the displaying apparatus 10 can be made consistent with the body direction of the subject 15 being displayed (i.e., the subject image) even if the subject 15 changes his body position. As a result, the user no longer feels a sense of discomfort in operating the magnetic guiding when the actual body direction of the subject 15 is inconsistent with the body direction of the subject 15 being displayed, and thus can operate the magnetic guiding of the capsule-shaped medical apparatus 2 inside the subject 15 (i.e., the capsule-shaped medical apparatus 2 which is difficult to be seen directly) intuitively and easily.

As described above, in the embodiment of the present invention, the subject image which shows the body direction of the subject and the capsule image which shows the position and the direction of the capsule-shaped medical apparatus inside the subject are displayed as the overlapped image on the displaying apparatus. When the magnetic guiding unit which magnetically guides the capsule-shaped medical apparatus inside the subject is operated, the coordinate system of the input operation direction of the operation unit which operates the magnetic guiding unit is made consistent with the coordinate system of the display screen of the displaying apparatus, and the coordinate information of the movement direction corresponding to the input operation direction which is input from the operation unit is transformed into the coordinate system of the magnetic guiding unit. Then the capsule-shaped medical apparatus inside the subject is magnetically guided in the direction which is specified by the transformed coordinate information. Thus, in the display screen of the displaying apparatus, the movement direction (the movement direction or the rotation direction) of the capsule image which is moved or rotated according to the magnetic guiding of the capsule-shaped medical apparatus can be made consistent with the input operation direction of the operation unit. As a result, even if the movement direction of the capsule image is different from the input operation direction of the operation unit, the user no longer feels the sense of discomfort during such operation. Thus, the capsule guiding system in which the user can avoid the sense of discomfort during the operation, and can operate the magnetic guiding of the capsule-shaped medical apparatus inside the subject (i.e., the capsule-shaped medical apparatus difficult to be seen directly) intuitively and easily can be realized.

Further, the correspondence relation between the movement direction of the capsule-shaped medical apparatus being magnetically guided and the input operation direction of the operation unit is determined based on the relative direction of the displaying apparatus to the magnetic guiding unit. Regardless of the relative position and direction of the displaying apparatus to the magnetic guiding unit, the movement direction of the capsule image being displayed on the displaying apparatus can be made consistent with the input operation direction of the operation unit. Thus, the sense of discomfort during the operation can be eliminated without exception, regardless of the relative direction of the displaying apparatus to the magnetic guiding unit.

Further, the relative direction of the displaying apparatus to the magnetic guiding unit is detected by the direction detecting unit, to change, according to the change of the detected relative direction of the displaying apparatus, the display information (the position locus information of the capsule-shaped medical apparatus) of the displaying apparatus, and also the correspondence relation between the movement direction of the capsule-shaped medical apparatus being magnetically guided and the input operation direction of the operation unit. Thus, even if the relative direction of the displaying apparatus to the magnetic guiding unit is changed, the movement direction of the capsule image being displayed on the displaying apparatus can be made consistent with the input operation direction of the operation unit. As a result, the displaying apparatus can be arranged in any relative direction from the magnetic guiding unit without causing the sense of discomfort.

The body position of the subject is detected by the body position detecting unit to change, according to the detected change of the body position of the subject, the position and the direction of the subject image and the capsule image being displayed on the displaying apparatus, and further the correspondence relation between the movement direction of the capsule-shaped medical apparatus being magnetically guided and the input operation direction of the operation unit. Thus, even if the subject containing the capsule-shaped medical apparatus inside his body changes his body position during the examination, the movement direction of the capsule image being displayed on the displaying apparatus can be made consistent with the input operation direction of the operation unit. As a result, the sense of discomfort can be eliminated without exception regardless of the body position of the subject.

The locus information which indicates the locus of the capsule-shaped medical apparatus inside the subject is displayed on the displaying apparatus. The position and the direction of the locus information as well as the subject image and the capsule image are changed according to the change of body position of the subject. Thus, even if the subject being examined changes his body position, the locus of the capsule-shaped medical apparatus inside the subject can be displayed correctly. As a result, the magnetic guiding of the capsule-shaped medical apparatus can be easily supported.

In the embodiment of the present invention, the subject 15 containing the capsule-shaped medical apparatus 2 inside his body changes the body position. Not limited to this, the body position of the subject 15 may be maintained being unchanged. In this case, the capsule guiding system 1 may not include the body position detecting unit 5 and the detection coils 5a to 5c.

Further, in the embodiment of the present invention, the relative direction of the displaying apparatus 10 to the magnetic guiding apparatus 6 is changed. Not limited to this, the relative direction of the displaying apparatus 10 to the magnetic guiding apparatus 6 (i.e., the direction to which the displaying apparatus 10 is arranged relatively from the magnetic guiding apparatus 6) may be maintained in a desired direction. In this case, the capsule guiding system 1 may not include the direction detecting unit 11 which detects the relative direction of the displaying apparatus 10.

Further, in the embodiment of the present invention, the relative direction of the displaying apparatus 10 to the magnetic guiding apparatus 6 is detected by the direction detecting unit 11. Not limited to this, information indicating the relative direction of the displaying apparatus 10 to the magnetic guiding apparatus 6 may be input to the control unit 13 via the input unit 9. In this case, based on the input information of the input unit 9 (the information which indicates the relative direction of the displaying apparatus 10 to the magnetic guiding apparatus 6), the guiding control unit 13b can determine the correspondence relation between the coordinate system of the display screen of the displaying apparatus 10 and the absolute coordinate system of the magnetic guiding apparatus 6, and the correspondence relation between the input operation direction of the operation unit 8 and the movement direction of the capsule-shaped medical apparatus 2 being magnetically guided.

Further, in the embodiment of the present invention, only one of the position-direction displaying units 10a to 10c and the image displaying unit 10d is selected as the operation screen, and the coordinate system of the selected operation screen is made consistent with the coordinate system of each input operation direction of the joysticks 8a, 8b. Not limited to this, two of the position-direction displaying units 10a to 10c and the image displaying unit 10d may be selected as the operation screens, and the coordinate systems of the two selected operation screens (any two screens of the position-direction displaying units 10a to 10c and the image displaying unit 10d) may be made consistent with the coordinate system of the input operation directions of the joysticks 8a, 8b, respectively. In this case, the joystick 8a inputs the operation information for the magnetic guiding corresponding to the input operation direction which is consistent with the coordinate system of a first operation screen of the two operation screens, and the joystick 8b inputs the operation information for the magnetic guiding corresponding to the input operation direction which is consistent with the coordinate system of a second operation screen of the two operation screens. The coordinate-transformation processing unit 13c transforms each of the coordinate information (the coordinate information which specifies the movement direction of the capsule-shaped medical apparatus 2) included in the two of the operation information which are input from the joysticks 8a, 8b into the absolute coordinate system of the magnetic guiding apparatus 6. The guiding control unit 13b combines the two of the transformed coordinate information to determine the three-dimensional movement direction of the capsule-shaped medical apparatus 2 in the absolute coordinate system, and controls the magnetic guiding which moves the capsule-shaped medical apparatus 2 in the determined three-dimensional movement direction.

Further, in the embodiment of the present invention, the horizontal directions of the in-vivo image P being displayed on the image displaying unit 10d are made consistent with the horizontal directions of the capsule-shaped medical apparatus 2. Not limited to this, the horizontal direction of the in-vivo image P being displayed on the image displaying unit 10d may be made consistent with the horizontal direction of the capsule-shaped medical apparatus 2 when the capsule-shaped medical apparatus 2 moves forward, whereas the horizontal direction of the in-vivo image P being displayed on the image displaying unit 10d may be inverted to be opposite to the horizontal direction of the capsule-shaped medical apparatus 2 when the capsule-shaped medical apparatus 2 moves backward. In this case, when the capsule-shaped medical apparatus 2 is rotated (especially, turned), the direction of change of the in-vivo image P being displaying on the image displaying unit 10d can be made consistent with the rotation direction of the capsule-shaped medical apparatus 2. As a result, inconsistency between the direction of change of the in-vivo image P and the input operation direction of the operation unit 8 can be avoided, whereby the sense of discomfort, which may arise during the operation when the image displaying unit 10d is selected as the operation screen, can be eliminated.

Further, in the embodiment of the present invention, the body position of the subject 15 is detected based on the detection of magnetic field. Not limited to this, an imaging device which captures the image of an appearance of the subject 15 at least from two directions may be arranged inside the magnetic guiding apparatus 6 instead of the detection coils 5a to 5c. The body position detecting unit 6 may detect the body position of the subject 15 based on the image of the appearance of the subject 15 captured from two directions by the imaging device.

Further, in the embodiment of the present invention, the subject images K1 to K3 which schematically shows the outer shape (body shape) of the subject 15 are displayed on the position-direction displaying units 10a to 10c, respectively. Not limited to this, the subject images displayed on the position-direction displaying units 10a to 10c may be images which schematically show digestive tracts inside the subject 15 through which the capsule-shaped medical apparatus 2 moves, or a combination of a schematic image of the outer shape of the subject 15 and a schematic image of the digestive tracts.

Further, in the embodiment of the present invention, the subject images K1 to K3 and the capsule images D1 to D3 are moved or rotated according to the magnetic guiding of the capsule-shaped medical apparatus 2. Not limited to this, the longitudinal direction of the capsule images D1 to D3 may be maintained relative to a predetermined direction (e.g., vertical direction, horizontal direction, or the like of the display screen) of the display screen of the displaying apparatus 10, and the relative position and the relative direction of the subject images K1 to K3 may be changed relatively to the capsule images D1 to D3. Alternatively, the body direction (longitudinal direction) of the subject images K1 to K3 may be maintained relative to the predetermined direction of the display screen of the displaying apparatus 10, and the relative position and the relative direction of the capsule images D1 to D3 may be changed relative to the subject images K1 to K3.

Further, in the embodiment of the present invention, the subject images K1 to K3 and the capsule images D1 to D3 are displayed on the position-direction displaying units 10a to 10c, respectively in a manner such that the subject 15 and the capsule-shaped medical apparatus 2 inside the subject 15 are displayed on the displaying apparatus from three different viewpoints. Not limited to this, three-dimensional images of the subject 15 and the capsule-shaped medical apparatus 2 inside the subject 15 which are viewed from a viewpoint at the side of the displaying apparatus 10 may be displayed on the displaying apparatus 10 as an overlapped image.

Further, in the embodiment of the present invention, the capsule-shaped medical apparatus 2 which captures the in-vivo image of the subject 15 is described. Not limited to this, the capsule-shaped medical apparatus of the capsule guiding system according to the present invention may be a capsule-shaped pH measuring apparatus which measures a pH value (an example of in-vivo information) inside the subject, a capsule-shaped drug introducing apparatus which spreads or injects drug inside the subject, or a capsule-shaped extracting apparatus which extracts a substance (an example of in-vivo information) inside the subject, as long as these apparatuses can be magnetically guided.

Further, in the embodiment of the present invention, the magnetic guiding of the capsule-shaped medical apparatus 2 is operated through the input operation of the two joysticks

8a, 8b. Not limited to this, two cross-shaped input buttons may be provided in the operation unit 8 instead of the joysticks 8a, 8b, and the magnetic guiding of the capsule-shaped medical apparatus 2 may be operated through input operation of the two input buttons.

Further, in the embodiment of the present invention, the capsule-shaped medical apparatus 2 is moved by attractive force and repulsive force of the magnetic field of the magnetic guiding apparatus 6. Not limited to this, spiral projection which forms spiral structure around the longitudinal axis of the capsule-shaped medical apparatus 2 may be formed on an outer wall surface of the cylinder-shaped container 20a, and the capsule-shaped medical apparatus 2 may be rotated around the longitudinal axis by the rotating magnetic field to be moved forward or backward.

Further, in the embodiment of the present invention, the position and the direction of the capsule-shaped medical apparatus 2 inside the subject 15 are detected based on the detection result of the guiding magnetic field released from the capsule-shaped medical apparatus 2. Not limited to this, sound waves (preferably, ultrasonic waves) may be transmitted to and received from the capsule-shaped medical apparatus 2 inside the subject 15. In this case, an echo signal from the capsule-shaped medical apparatus 2 is detected, and the position and the direction of the capsule-shaped medical apparatus 2 inside the subject 15 are detected based on the detected echo signal. Further, the position and the direction of the capsule-shaped medical apparatus 2 inside the subject 15 may be detected using X-ray image data of the inside of the subject 15.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule guiding system comprising:
   a magnetic guiding unit which guides a capsule-shaped medical apparatus adapted to be introduced inside a subject by magnetic force;
   a displaying unit which displays a subject image showing the subject and a capsule image showing the capsule-shaped medical apparatus as an overlapped image, and changes a relative position or a relative direction of the subject image and the capsule image according to a guiding of the capsule-shaped medical apparatus performed by the magnetic guiding unit;
   an operation unit which inputs coordinate information specifying a movement direction of the capsule-shaped medical apparatus, and operates the guiding of the capsule-shaped medical apparatus performed by the magnetic guiding unit;
   a control unit which adjusts a coordinate system of a display screen of the displaying unit and a coordinate system of an input operation direction of the operation unit to be consistent with each other, performs a coordinate transformation which transforms the coordinate information input by the operation unit into the coordinate system of the magnetic guiding unit, and controls the guiding of the capsule-shaped medical apparatus based on the coordinate information on which the coordinate transformation is performed;
   a body position detecting unit which detects a body direction of the subject; and
   a direction detecting unit which detects the relative direction of the displaying unit to the magnetic guiding unit; wherein
   the control unit determines a correspondence relation between the input operation direction of the operation unit and the movement direction of the capsule-shaped medical apparatus based on a relative direction of the displaying unit to the magnetic guiding unit;
   the control unit changes the correspondence relation between the input operation direction of the operation unit and the movement direction of the capsule-shaped medical apparatus according to change of the relative direction of the displaying unit detected by the direction detecting unit; and
   the control unit keeps the body direction of the subject viewed from the displaying unit consistent with a body direction of the subject on the display screen, and keeps a horizontal input operation direction of the operation unit consistent with a horizontal direction of the display screen.

2. The capsule guiding system according to claim 1, wherein
   the displaying unit includes plural different-viewpoint displaying units which display subject images and capsule images viewed from viewpoints which differ from each other,
   the operation unit includes two input units which input the coordinate information specifying the three-dimensional movement direction of the capsule-shaped medical apparatus, and
   the control unit adjusts the coordinate system of one or two of the different-viewpoint displaying units and the coordinate systems of the input operation directions of the two input units to be consistent with each other, performs the coordinate transformation which transforms each coordinate information input by the input units into the coordinate system of the magnetic guiding unit, and controls the guiding of the capsule-shaped medical apparatus based on each coordinate information on which the coordinate transformation is performed.

3. The capsule guiding system according to claim 2, wherein
   images displayed on the plural different-viewpoint displaying units are images viewed in three orthogonal axes; and
   the operation unit includes a selecting unit which selects an image from among the images displayed on the different-viewpoint displaying units whose coordinate system is to be made consistent with the coordinate system of the input operation direction of the two input units.

4. The capsule guiding system according to claim 1, wherein the body position detecting unit is configured to further detect a body position of the subject, wherein
   the control unit changes the correspondence relation between the input operation direction of the operation unit and the movement direction of the capsule-shaped medical apparatus according to change of the body position of the subject detected by the body position detecting unit.

5. The capsule guiding system according to claim 4, wherein the displaying unit changes a position or a direction of the subject image and the capsule image according to the change of body position of the subject detected by the body position detecting unit.

6. The capsule guiding system according to claim 4, wherein the displaying unit displays a locus of the capsule-shaped medical apparatus inside the subject, and changes a direction of the locus according to the change of body position of the subject detected by the body position detecting unit.

7. The capsule guiding system according to claim 1, wherein the direction detecting unit detects the relative direction of the displaying unit to the magnetic guiding unit by detecting a magnetic field released by the magnetic guiding unit.

* * * * *